Figure 2:
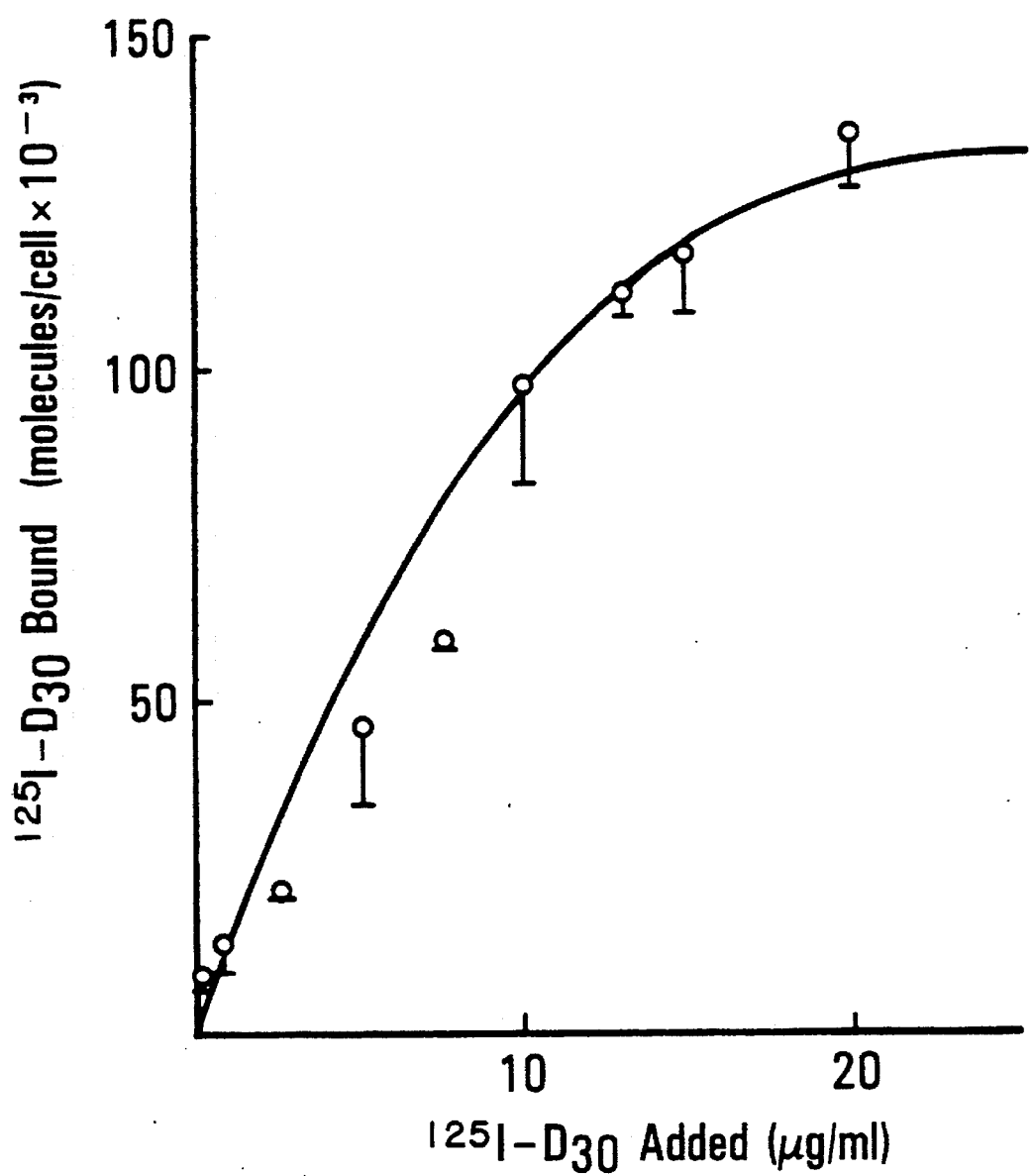

United States Patent [19]

Altieri et al.

[11] Patent Number: 5,473,051
[45] Date of Patent: Dec. 5, 1995

[54] INHIBITION OF MAC-1 RECEPTOR BINDING TO FIBRINOGEN USING $D_{30}$ HOMOLOGS

[75] Inventors: Dario C. Altieri, La Jolla; Edward F. Plow, San Diego; Thomas S. Edgington, La Jolla, all of Calif.

[73] Assignee: The Scripps Research Institute, La Jolla, Calif.

[21] Appl. No.: 734,296

[22] Filed: Jul. 18, 1991

Related U.S. Application Data

[63] Continuation-in-part of Ser. No. 556,643, Jul. 19, 1990.
[51] Int. Cl.$^6$ .............................. C07K 14/75; C07K 7/06
[52] U.S. Cl. ..................... 530/382; 530/350; 530/326; 530/327; 530/328
[58] Field of Search .............................. 514/12; 530/350, 530/326, 327, 328, 382

[56] References Cited

U.S. PATENT DOCUMENTS 4,650,678  3/1987  Fuhge et al. ............................ 424/101

OTHER PUBLICATIONS

Furlan et al., *Biochim. et Biophys. Acta.*, 400:95–111 (1975).
Doolittle et al., *Nature*, 280:464–468 (1979).
Fair et al., *J. Biol. Chem.*, 256:8018–8023 (1981).
Altieri et al., *J. Clin. Invest.*, 78:968–976 (1986).
Price et al., *J. Immunol.*, 139:4174–4177 (1987).
Altieri et al., *J. Cell. Biol.*, 107:1893–1900 (1988).

*Primary Examiner*—Michael P. Woodward
*Attorney, Agent, or Firm*—April C. Logan

[57] ABSTRACT

The present invention contemplates therapeutic compositions containing a $D_{30}$ homolog capable of binding to the Mac-1 receptor $D_{30}$ binding site and inhibiting fibrinogen binding to the Mac-1 receptor via the $D_{30}$ binding site, Methods of inhibiting Mac-1 receptor binding to any Mac-1 ligand and methods of inhibiting Mac-1 receptor mediated inflammation within a patient by administering a $D_{30}$ homolog are also contemplated,

2 Claims, 9 Drawing Sheets

| | |
|---|---|
| 1 | ADSGEGDFLAEGGGVRGPRVVERHQSACKD |
| 31 | SDWPFCSDEDWNYKCPSGCRMKGLIDEVNQ |
| 61 | DFTNRINKLKNSLFEYQKNNKDSHSLTTNI |
| 91 | MEILRGDFSSANNRDNTYNRVSEDLRSRIE |
| 121 | VLKRKVIQKVQHIQLLQKNVRAQLVDMKRL |
| 151 | EVDIDIKIRSCRGSCSRALAREVDLKNYED |
| 181 | QQKQLEQVIAKDLLPSRDRQHLPLIKMKPV |
| 211 | PNLVPGNFKSQLQKVPPEWKALTDMPQMRM |
| 241 | ELERPGGNEITRGGSTSYGTGSETESPRNP |
| 271 | SSAGSWNSGSSGPGSTGNRNPGSSGTGSGA |
| 301 | TWKPGSSGPGSTGSWNSGSSGTGSTGNQNP |
| 331 | GSPRPGSTGTWNPGSSERGSAGHWTSESSV |
| 361 | SGSTGQWHSESGSFRPDSPGSGNARPNDPN |
| 391 | WGTFEEVSGNVSPGTRREYHTEKLVTSKGD |
| 421 | KELRTGKEKVTSGSTTTTRRSCSKTVTKTV |
| 451 | IGPDGHKEVTKEVVTSEDGSDCPEAMDLGT |
| 481 | LSGIGTLDGFRHRHPDEAAFFDTASTGKTF |
| 511 | PGFFSPMLGEFVSETESRGSESGIFTNTKE |
| 541 | SSSHHPGIAEFPSRGKSSSYSKQFTSSTSY |
| 571 | NRGDSTFESKSYKMADEAGSEADHEGTHST |
| 601 | KRGHAKSRPV |

FIG. IA

α   ADSGEGDFLAEGGGVRGPRVVERHQSA
β     QGVNDNEEGFFSARGHRPLDKKREEAPSLRPAPPPISGGGYRARPA
γ

α           CKDSDWPFC  SDEDWNYKCPSGCRMKGLIDEVNQDFT
β   KAAATQKKVERKAPDAGGCLHADPDLGVLCPTGCQLEALLQQERPIR
γ              YVATRDNCCILDERFGSYCPTTCGIADFLSTYQTKVD

α   NRINKLKNSLFEYQKNNK DSHSLTTNIMEILRGDFSSANNRDNTYNR
β   NSVDELNNNVEAVSQTSSSSQFYMYLLKDLWQKRQKQVKDNENVVNEY
γ   KDLQSLEDILHQVENKTS EVKQLIKAIQLTYNPDESSKPNMIDAATL

α   VSEDLRSRIEVLKRKVIQKVQHIQLLEKNVRAQLVDMKRLEVDIDIKI
β   SSELEKHQLYIDETVNSNIPTNLRVLRSILENLRSKIQKLESDVSAQM
γ   KSRKMLEEIMKYEASILTHDSSIRYLQEIYNSNNQKIVNLKEKVAQLE

α   RSCRGSCSRALAREVDLKNYEDQQKQLEQVIAKDLLPSRDRQHLPLIK
β   EYCRTPCTVSCDIPVVSG     KECEEIIRKGGETSEMYLIQPDSS
γ   AQCQEPCKDTVQIHDITG     KDCQDIANKGAKQSGLYFIKPLKA

α   MKPVPNLVPGNFKSQLQKVPPEWKALTDMPQMRM
β   VKPYRVYCDMNTENGGWTVIQNRQDGSVDFGRKWDPYKQGFGNV ATN
γ   NQQFLVYCEIDGSGNGWTVFQKRLDGSVDFKKNWIQYKEGFGHLSPTG

FIG. IB-1

```
α           ELERPGGNEITRGGSTSYGTGSETESPRNPSSAGS
β  TDGKBYCGLPGEYWLGBBKISELTRMGPTELLI    EMEDWKGDKVKAH
γ  TT           EFWLGNEKIHLISTQSAIPYALRVELEDWNGRTSTAD

α  WNSGSSGPGSTGNRNPGSSGTGSGATWKPGSSGPGSTGSWNSGSSGTG
β  YGGFTVQNEANKYQISVNKYRGTAGNA
γ  YAMFKVGPEADKYRLTYAYFAGGDAGD

α  STGNQNPGSPRPGSTGTWNPGSSERGSAGHWTSESSVSGSTGQWHSES
β
γ

α  GSFRPDSPGSGNARPNDPNWGTFEEVSGNVSPGTRREYHTEKLVTSKG
β                              LMDGASQL  MGENRTMTIHN
γ                              AFDGFDFGDDPSDKFFTSHN

α  DKELRTGKEKVTSGSTTTTRRSCSKTVTKTVIGPDGHKEVTKEVVTSE
β  GMFFSTYDRDNDGWLTSDPRKQCSKEDGGGWWYBRCHAANPNGRYYWG
γ  GMQFSTWDNDNDKFEGN    CAEQDGSGWWMNKCHAGHLNGVYYQG

α  DGSDCPEAMDLGTLSGIGTLDGFRHRHPDEAAFFDTASTGKTFPGFFS
β  GQYTWDMAKHGTBDGVVWMNWKGSWYSMRKMSM       KIRPFFPQ
γ  GTYSKASTPNGYDNGIIWAT  KTRWYSMKKTTM      KIIPFNRL
```

FIG. IB-2

```
α  PMLGEFVSETESRGSESGIFTNTKESSSHHPGIAEFPSRGKSSSYSKQ
β  Q
γ  TIGEGQQHHLGGAKQAGDV

α  FTSSTSYNRGDSTFESKSYKMADEAGSEADHEGTHSTKRGHAKSRPV
β
γ
```

FIG. IB-3

INHIBITION OF MAC-1 RECEPTOR BINDING TO FIBRINOGEN USING $D_{30}$ HOMOLOGS

This invention was made with the support of the Government of the United States of America, and the Government of the United States of America has certain rights in the invention.

CROSS-REFERENCE TO RELATED APPLICATION

The present application is a continuation-in-part of application Ser. No. 07/556,643 filed Jul. 19, 1990, which disclosure is herein incorporated by reference.

TECHNICAL FIELD

The present invention contemplates the use of a $D_{30}$ homolog to inhibit Mac-1 receptor fibrinogen binding and the use of Mac-1 receptors and antibodies against $D_{30}$ homolog containing complexes in diagnostic systems and assay methods.

BACKGROUND

Integrins are a functionally and structurally related group of receptors that interact with a wide variety of ligands including extracellular matrix glycoproteins, complement and other cells. Integrins participate in cell-matrix and cell-cell adhesion in many physiologically important processes including embryological development, hemostasis, thrombosis, wound healing immune and nonimmune defense mechanisms and oncogenic transformation. See Hynes, *Cell*, 48:549–554 (1987). The majority of integrins participating in dynamic cell adhesion, bind a tripeptide, arginine-glycine-aspartic acid (RGD), present in their ligand, causing cell adhesion. See Ruoslahti et al., *Science*, 238:491–497 (1987).

Mac-1 (CD11b/CD18) is an integrin receptor found predominantly on macrophages and granulocytes. Like all integrin receptors, Mac-1 is a heterodimeric, transmembrane glycoprotein composed of non-covalently associated alpha and beta subunits.

The alpha ($\alpha$) and beta ($\beta$) chains of Mac-1 have molecular weight of 170,000 and 95,000 daltons, respectively, and the Mac-1 $\alpha$ chain has been completely sequenced. See Corbi et al., *J. Biol. Chem.*, 263:12403–12411 (1988). For a review of the integrin receptors, see Hynes, *Cell*, 48:549–554 (1987) . .

Mac-1 mediates neutrophil/monocyte adhesion to vascular endothelium and phagocytosis of complement-opsonized particles. Antibodies to the Mac-1 receptor alter neutrophil function in vivo including inhibiting neutrophil migration into inflammatory sites. See Price et al., *J. Immunol.*, 139:4174–4177 (1987). Mac1 also functions as a receptor for fibrinogen in a reaction linked to fibrin deposition on the monocyte surface. See Altieri et al., *J. Cell Biol.*, 107:1893–1900 (1988); Wright et al., *Proc. Natl. Acad. Sci. USA*, 85:7734–7738 (1988); Trezzini et al., *Biochem. Biophys. Res. Commun.*, 156:477–484 (1988) and Gustafson et al., *J. Cell Biol.*, 109:377–387 (1989).

Fibrinogen is a complex molecule of approximately 340,000 daltons and consists of three pairs of subunit polypeptides, called the $\alpha$, $\beta$ and gamma chains. These individual chains are held together by several disulfide bonds. The proteolytic digestion of fibrinogen by plasmin produces fragments A, B, C, D and E, all having a molecular weight of less the 85,000 daltons. See Pizzo et al., *J. Biol. Chem.*, 247:636–645 (1972).

Further proteolytic digestion of fibrinogen by plasmin produces a $D_{30}$ fragment with a molecular weight of about 30,000 daltons containing portions of the $\alpha$, $\beta$ and gamma chains of fibrinogen. See Furlan et al., *Biochim. Biophys. Acta*, 400:95–111 (1975).

The deposition of fibrinogen on the leukocyte surface occurs in a variety of inflammatory responses such as delayed type hypersensitivity, incompatible transplant rejection and the physiopathology of vascular obstruction and atherogenesis. See Geczy et al., *J. Immunol.*, 130:2743–2749 (1983); Hooper et al., *J. Immunol.*, 126:1052–1058 (1981); Colvin et al., *J. Immunol.*, 114:377–387 (1975); Hattler et al., *Cell Immunology*, 9:289–295 (1973); Gerrity, R. G., *Am. J. Pathol.*, 103:181–190 (1981) and *Am. J. Pathol.*, 103:191–200 (1981); and Shelley et al., *Nature*, 270:343–344 (1977).

Recently, the interaction of fibrinogen with the Mac-1 receptor of leukocytes has been postulated to be a dynamic cell adhesion reaction involving the recognition of the tripeptide RGD within fibrinogen by the Mac-1 receptor similar to the interaction of fibrinogen with the integrin receptors on platelets and endothelial cells. See Altieri et al., *J. Clinic Invest.*, 78:968–976 (1986); Pytela et al., *Science*, 231:1559–1562 (1986) and Ruoslahti et al., *Science*, 238:491–497 (1987) and *Cell*, 44:517–518 (1986).

BRIEF DESCRIPTION OF THE INVENTION

It has now been discovered that the Mac-1 receptor binds fibrinogen at a site within the $D_{30}$ fragment of fibrinogen and that the Mac-1 receptor does not bind the $D_{30}$ fragment via the tripeptide, RGD. A specific region of $D_{30}$ that binds Mac-1 has been identified.

Thus, the invention describes a fibrinogen gamma chain derived polypeptide ($D_{30}$ polypeptide) that includes an amino acid residue sequence according to the formula:— QKRLDGS— that binds Mac-1 and inhibits $D_{30}$ binding to Mac-1, said sequence shown in SEQ ID NO 3 from residue 195 to residue 201. Preferably, the polypeptide has a sequence that corresponds to the amino acid residue sequence of the gamma chain of fibrinogen.

The invention also describes an anti-$D_{30}$ receptor binding site specific antibody comprising antibody molecules that preferably immunoreact with a $D_{30}$ polypeptide of this invention.

The present invention also contemplates compositions containing a therapeutically effective amount of a $D_{30}$ homolog or anti-$D_{30}$ receptor binding site specific antibody capable of binding to the Mac-1 $D_{30}$ binding site and inhibiting fibrinogen binding to the Mac-1 $D_{30}$ binding site.

The present invention contemplates the use of a $D_0$ homolog or anti-$D_{30}$ receptor binding site specific antibody to inhibit Mac-1 receptor-mediated binding and inflammation in a patient by administering a therapeutically effective amount of a $D_{30}$ homolog or a $D_{30}$ homolog containing composition to the patient.

Also contemplated by the present invention is an anti-($D_{30}$ idiotype) antibody that is capable of binding to the Mac-1 $D_{30}$ binding site and inhibiting $D_{30}$ binding to the Mac-1 binding site.

The invention contemplates the use of an anti-($D_{30}$ idiotype) antibody to inhibit Mac-1 receptor-mediated binding and inflammation in a patient by administering a therapeutically effective amount of an anti-($D_{30}$ idiotype) antibody or a composition containing an anti-($D_{30}$ idiotype) antibody to the patient.

Also contemplated by the present invention are methods of detecting the presence of a $D_{30}$ homolog within liquid composition using either Mac-1 receptors or an anti-$D_{30}$ antibody.

The present invention contemplates the detection of a Mac-1 receptor:$D_{30}$ homolog complex within a liquid composition such as blood or blood derived products.

The present invention also contemplates a method of detecting cells having a Mac-1 receptor in vivo by administering to a patient a composition containing a $D_{30}$ homolog linked to an in vivo indicating means that is capable of effectively binding to the patient's Mac-1 receptors.

BRIEF DESCRIPTION OF THE DRAWINGS

In the drawings, forming a portion of this disclosure:

FIG. 1, containing FIGS. 1A and 1B–1 through 1B–3, illustrates the amino acid residue sequences of the α, β and gamma chains of human fibrinogen described by Doolittle et al., *Nature*, 280:464–469 (1979).

FIG. 1A illustrates the complete amino acid residue sequence of the α-chain of human fibrinogen (SEQ ID NO 1). The position in the amino acid residue sequence of the left-hand most residue is indicated by the numbers in the left margin of the figure. The N-terminus of the A chain remnant (αs) of $D_{30}$ originates with amino acid residues $Leu^{136}$, $Lys^{138}$ and $Asn^{139}$. The αs chain remnant of $D_{30}$ does not contain the amino acid residues $Arg^{95}$, $Gly^{96}$, and $Asp^{97}$ (RGD) or the amino acid residues $Arg^{572}$, $Gly^{573}$ and $Asp^{574}$ (RGD).

FIGS. 1B–1, 1B–2, and 1B–3 illustrate the comparison of the α chain amino acid residue sequences with amino acid residue sequences of the β- and gamma-chains of human fibrinogen listed as SEQ ID NO 1, 2 AND 3, respectively. Significant homology exists among all three chains over the first 210 amino acid residues. Underlined amino acid residues denote matched identical amino acid residues between the α, β and gamma chains. The origin of $D_{30}$ in the B chain remnant (Bβ) is assigned at amino acid residues $Asp^{134}$ (D), $Asn^{135}$ β(N), $Glu^{13}$ (E), and $Asn^{137}$ (N) in boxed area. The origin of $D_{30}$ in the gamma chain is assigned at amino acid residues $Met^{89}$ (M), $Leu^{90}$ (L), $Glu^{91}$ (E), and $Glu^{92}$ (E) in boxed area.

FIG. 2 illustrates the binding curve of increasing concentrations of $^{125}I$-$D_{30}$ to stimulated polymorphonuclear cells (neutrophils). Specific binding is calculated in the presence of 100-fold molar excess unlabelled fibrinogen or $D_{30}$ and is subtracted from the total to calculate the specific binding depicted in the curve by open circles. Each point is the mean±standard error of the mean (SEM) of three independent experiments. Neutrophils bind $^{125}I$-$D_{30}$ in a specific and saturable reaction approaching steady state at 15–20 g/ml of added $^{125}I$-$D_{30}$.

FIG. 3 illustrates the effects of increasing concentrations of fibrinogen and fibrinogen fragments X, D:E, and D on competing the binding of $^{125}I$-fibrinogen to stimulated neutrophils. Fibrinogen, fibrinogen fragments X, D:E, D, and RGD are, respectively, denoted by open circles, closed circles, open squares, closed squares and triangles. Competition by the added unlabelled competitors is measured as the percent of $^{125}I$-fibrinogen bound as compared to control $^{125}I$-fibrinogen bound in the absence of competitors. The data is calculated as described in FIG. 2. Fibrinogen and fibrinogen fragments compete the binding of $^{125}I$ fibrinogen to neutrophils whereas RGD does not.

FIG. 4 illustrates the effects of increasing concentrations of fibrinogen fragments $D_{30}$, represented by closed circles and fragment E, represented by open circles on the competing of binding of $^{125}I$-fibrinogen to stimulated neutrophils. Competition is measured as described in FIG. 3 and the data is calculated as described in FIG. 2. Increasing concentrations of $D_{30}$ produce dose-dependent inhibition of $^{125}I$-fibrinogen binding to stimulated neutrophils whereas fragment E does not.

FIG. 5 illustrates the specific binding of the synthetic polypeptide P1 derived from the gamma chain of $D_{30}$ to monocytes. The amount of radiolabelled P1 polypeptide bound to monocytes in cpm X1000 is plotted on the ordinate against time in 10 minute intervals up to one hour. The binding of radiolabelled P1 measured in the presence of unlabelled P1 as indicated by the line with solid diamonds was compared to that in the presence of an irrelevant polypeptide, L10, as indicated by the line with open squares. The binding assay was performed as described in Example 8D and the data was calculated as described in FIG. 2. The binding of P1 to monocytes increases over time in the presence of L10 while it is competitively inhibited in the presence of cold P1.

FIG. 6 illustrates the specific binding of P1 to THP-1 cells in the presence of various competitive inhibitors including $D_{30}$, the irrelevant L10 polypeptide, a monoclonal antibody IB4 which recognizes the beta subunit of the integrin receptor Mac-1 on THP-1 cells, a monoclonal antibody M1/70 which recognizes the alpha subunit of Mac-1, and lastly a polyclonal antibody against tissue factor (TF). The binding assay is performed as described in Example 8D and the data was calculated as described in FIG. 2. The amount of radiolabelled P1 bound to THP-1 cells is plotted in a bar graph format in cpm X1000. $D_{30}$, IB4 and M1/70 competitively inhibited the binding of P1 to THP-1 cells thus confirming that P1 contains the receptor-binding site of fibrinogen which binds to the Mac-1 receptor on those cells.

FIG. 7 illustrates the competitive inhibition of fibrinogen binding to THP-1 cells by P1 polypeptide compared to the lack of inhibition by the irrelevant polypeptide L10. The competitive inhibition assay was performed as described in Example 8C and the data was calculated as described in FIG. 2. The amount of radiolabelled fibrinogen bound to THP-1 cells is plotted on the ordinate as molecules/cell X1000 against increasing concentrations of polypeptide in μg/ml. Maximal inhibition of fibrinogen binding to THP-1 cells was achieved with 20 μg/ml P1 polypeptide.

DETAILED DESCRIPTION OF THE INVENTION

A. Definitions

Amino Acid Residue: The amino acid residues described herein are preferred to be in the "L" isomeric form. However, residues in the "D" isomeric form can be substituted for any L-amino acid residue, as long as the desired functional property is retained by the polypeptide. $NH_2$ refers to the free amino group present at the amino terminus of a polypeptide. COOH refers to the free carboxyl group present at the carboxy terminus of the polypeptide. In keeping with standard polypeptide nomenclature, *J. Biol. Chem.*, 243:3557–59, (1969), and adapted at 37 CFR1,822(b) (2), abbreviations for amino acid residues are as shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| Z | Glx | Glu and/or Gln |
| W | Try | tryptophan |
| R | Arg | arginine |
| D | Asp | aspartic acid |
| N | Asn | asparagine |
| B | Asx | Asn and/or Asp |
| C | Cys | cysteine |
| X | Xaa | Unknown or other |

It should be noted that all amino acid residue sequences are represented herein by formulae whose left to right orientation is in the conventional direction of amino-terminus to carboxy-terminus. Furthermore, it should be noted that a dash at the beginning or end of an amino acid residue sequence indicates a peptide bond to a further sequence of one or more amino acid residues, or to an amino-terminal $NH_2$ group or to a carboxy-terminal COOH group.

Polypeptide and Peptide: Polypeptide and peptide are terms used interchangeably herein to designate a linear series of amino acid residues connected one to the other by peptide bonds between the alpha-amino and carboxy groups of adjacent residues.

Receptor: Receptor and receptor protein are terms used herein to indicate a biologically active proteinaceous molecule that specifically (nonrandomly) binds to (or with) other molecules, referred to as ligands, to form a receptor-ligand protein complex. A representative receptor is the Mac-1 (CD11b/CD18) molecule present on monocytes.

Ligand: Ligand refers to a molecule that contains a structural portion that is bound by specific interaction with a particular receptor protein. A representative ligand is the $D_{30}$ fragment of fibrinogen.

Antibody: The term antibody in its various grammatical form is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules and portions of an immunoglobulin molecule, including those portions known in the art as Fab, Fab'F(ab')$_2$ and F(v)

Antibody Combining Site: An antibody combining site is that structural portion of an antibody molecule comprised of a heavy and light chain variable and hypervariable regions that specifically binds (immunoreacts with) an antigen. The term immunoreact in its various forms means specific binding between an antigenic determinant-containing molecule and a molecule containing an antibody combining site such as a whole antibody molecule or a portion thereof.

Monoclonal Antibody: The phrase monoclonal antibody in its various grammatical forms refers to a population of antibody molecules that contains only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen, e.g., a bispecific monoclonal antibody.

B. $D_{30}$ Homologs $D_{30}$ is a fragment of fibrinogen produced by proteolytic digestion of fibrinogen. The preparation of $D_{30}$ has been described by Fair et al., *J. Biol. Chem.*, 256:8018–8023 (1981), Furlaw et al., *Biochem. Biophys. Acta.*, 400:95–11) (1975) and in Example 1C. $D_{30}$ contains partially degraded β and gamma chains and extensively degraded α chains combined by inter-chain disulfide bonds as described by Pizzo et al., *J. Biol. Chem.*, 247:636–645 (1972). All references and documents cited in this application are hereby incorporated by reference.

The N-terminus of the Aαchain remnant of $D_{30}$ originates with amino acid residues $Leu^{136}$, $Gln^{137}$, $Lys^{138}$ and $Asn^{139}$ shown in FIG. 1A and using the amino acid sequence of the alpha chain described by Doolittle et al.; *Nature*, 280:464–469 (1979).

The Aαchain remnant of $D_{30}$ does not contain amino acid residues $Arg^{95}$, $Gly^{96}$ and $Asp^{97}$ (RGD) FIG. 1A) or the amino acid residues $Arg^{572}$, $Gly^{573}$ and $Asp^{574}$ (RGD) and has a Mw of about 11 to 13 kilodaltons (kDa). The N-termini of the β chain of $D_{30}$ contains amino acid residues $Asp^{134}$, $Asn^{135}Glu^{136}$, and $Asn^{137}$ (FIGS. 1B–1 through 1B–3). The N-terminus of the gamma of $D_{30}$ contains amino acid residues $Met^{89}$, $Leu^{90}$, $Glu^{91}$, and $Glu^{92}$ (FIGS. 1B–1 through 1B–3).

A $D_{30}$ homolog of the present invention is a polypeptide or protein capable of binding to the Mac-1 receptor at the $D_{30}$ binding site (i.e., the Mac-1 $D_{30}$ binding site) and inhibiting $D_{30}$ binding to the Mac-1 $D_{30}$ binding site. $D_{30}$ homologs include fibrinogen, portions of fibrinogen, $D_{30}$, portions of $D_{30}$, polypeptides homologous to a portion of $D_{30}$ or fibrinogen (i.e., a $D_{30}$ polypeptide), anti-idiotype antibodies having the internal image of the Mac-1 $D_{30}$ binding site [i.e., an anti-($D_{30}$ idiotype) antibody], polypeptides or protein homologous to $D_{30}$ or fibrinogen containing non-natural amino acid derivatives or non-proteinaceous side chains, chemical derivatives of either $D_{30}$, fibrinogen, fragments or polypeptides thereof, and conjugates containing a $D_{30}$ homolog.

As used herein, the phrase "$D_{30}$ polypeptide" refers to a polypeptide having an amino acid residue sequence that comprises an amino acid residue sequence that corresponds, and preferably is identical, to a portion of the $D_{30}$ region of the gamma chain of the fibrinogen molecule. The amino acid residue sequence of the gamma chain of fibrinogen is listed as SEQ ID NO 3 in the sequence listing. Preferably, a D30 polypeptide of the present invention has the capacity to inhibit $D_{30}$ binding to the Mac-1 $D_{30}$ binding site.

A $D_{30}$ polypeptide is preferably no more than about 150 amino acid residues in length for reasons of ease of synthesis and ability to direct the inhibition capacity to a precise contact site on $D_{30}$. Thus, it more preferred that a $D_{30}$ polypeptide be no more that about 100 amino acid residues, still more preferably no more than about 50 residues, and most preferably less than 20 amino acid residues in length.

A $D_{30}$ polypeptide of the present invention has an amino acid residues sequence that includes an amino acid residue sequence represented by the formula:

—QKRLDGS—, said sequence shown in SEQ ID NO 3 from residue 195 to residue 201.

The SEQ ID NO and corresponding residues of a described amino acid residue sequence are conveniently described herein in parenthesis, where the first number is the SEQ ID NO and the range following the colon represents the residue numbers of the indicated amino acid residues in the sequence listing. For example, "(3: 195–201)" refers to the sequence QKRLDGS shown in SEQ ID NO 3.

In preferred embodiments, a $D_{30}$ polypeptide has an amino acid residue sequence, the SEQ ID NO and residues corresponding to the fibrinogen gamma chain of which are shown in parenthesis, represented by a formula selected from the group consisting of:

QKRLDGSVDFKK, (3: 195–206)

GQKRLDGSVDFKK, (11: 195–206)

WTVFQKRLDGSV, (3: 191–202)

GQKRLDGS, (11: 195–201)

KYGWTVFQKRLDGSV, and (12: 191–202)

KYGQKRLDGS. (13: 195–201)

Preferably, a $D_{30}$ polypeptide of this invention is further characterized by its ability to immunologically mimic an epitope (antigenic determinant) expressed by $D_{30}$. Such a polypeptide is useful herein as a component in an inoculum for producing antibodies that immunoreact with $D_{30}$ or a $D_{30}$ homolog.

As used herein, the phrase "immunologically mimic" in its various grammatical forms refers to the ability of an $D_{30}$ polypeptide of this invention to immunoreact with an antibody of the present invention as defined herein.

It should be understood that a subject polypeptide need not be identical to the amino acid residue sequence of the gamma chain of fibrinogen, so long as it includes the required sequence and is able to function as a $D_{30}$ homolog as described herein.

A subject polypeptide includes any analog, fragment or chemical derivative of a polypeptide whose amino acid residue sequence is shown herein so long as the polypeptide is capable of inhibiting $D_{30}$ binding to the Mac-1 $D_{30}$ binding site. Therefore, a present polypeptide can be subject to various changes, substitutions, insertions, and deletions where such changes provide for certain advantages in its use. In this regard, a $D_{30}$ polypeptide of this invention corresponds to, rather than is identical to, the sequence of the gamma chain of fibrinogen where one or more changes are made and the polypeptide retains the function of a $D_{30}$ homolog in one or more of the assays as defined herein.

The term "analog" includes any polypeptide having an amino acid residue sequence substantially identical to a sequence specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Exemplary substitutions can be seen in several of the inhibitory $D_{30}$ polypeptides described herein having sequences that are not identical to the sequence of the gamma chain of fibrinogen.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form 0-acyl or 0-alkyl derivatives. The imidazole nitrogen of histidine may be derivatized to form N-im-benzylhistidine. Also included as chemical derivatives are those peptides which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted or serine; and ornithine may be substituted for lysine. Polypeptides of the present invention also include any polypeptide having one or more additions and/or deletions or residues relative to the sequence of a polypeptide whose sequence is shown herein, so long as the requisite binding activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of the gamma chain of fibrinogen, it is typically because one or more conservative or non-conservative substitutions have been made, usually no more than about 30 number percent, more usually no more than 20 number percent, and preferably no more than 10 number percent of the amino acid residues are substituted. Additional residues may also be added at either terminus for the purpose of providing a "linker" by which the polypeptides of this invention can be conveniently affixed to a label or solid matrix, or carrier. Preferably the linker residues do not form $D_{30}$ epitopes, i.e., are not similar in structure to the $D_{30}$.

Labels, solid matrices and carriers that can be used with the polypeptides of this invention are described hereinbelow.

Amino acid residue linkers are usually at least one residue and can be 40 or more residues, more often 1 to 10 residues, but do not form $D_{30}$ epitopes. Typical amino acid residues used for linking are tyrosine, cysteine, lysine, glutamic and aspartic acid, or the like. In addition, a subject polypeptide can differ, unless otherwise specified, from the natural sequence of the gamma chain of fibrinogen by the sequence being modified by terminal-$NH_2$ acylation, e.g., acetylation, or thioglycolic acid amidation, by terminal-carboxlyamidation, e.g., with ammonia, methylamine, and the like.

A polypeptide of the present invention can be prepared using the solid-phase synthetic technique initially described by Merrifield, *J. Am. Chem. Soc.*, 85:2149–2154 (1963).

Other polypeptide synthesis techniques may be found, for example, in M. Bodanszky et al., *Peptide Synthesis*, John Wiley & Sons, 2d Ed., (1976) as well as in other reference works known to those skilled in the art. A summary of polypeptide synthesis techniques may be found in J. Stuart and J. D. Young, *Solid Phase Peptide Synthesis*, Pierce Chemical Company, Rockford, Ill. 3d Ed., Neurath, H. et al., Eds., p. 104–237, Academic Press, N.Y. (1976). Appropriate protective groups for use in such syntheses will be found in the above texts as well as in J. F. W. McOmie, *Protective Groups in Organic Chemistry*, Plenum Press, New York, N.Y. (1973).

In general, those synthetic methods comprise the sequential addition of one or more amino acid residues or suitably protected amino acid residues to a growing polypeptide chain. Normally, either the amino or carboxyl group of the first amino acid residue is protected by a suitable, selectively removable protecting group is utilized for amino acids containing a reactive side group such as lysine.

Using a solid phase synthesis as an example, the protected or derivatized amino acid is attached to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amid linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence any remaining terminal and side group protecting groups (and solid support) are removed sequentially or concurrently, to provide the final polypeptide.

The Mac-1 $D_{30}$ binding site is the portion of the human leukocyte adhesion glycoprotein Mac-1 (CD11b/CD18) that binds to the $D_{30}$ fragment of fibrinogen. The Mac-1 $D_{30}$ binding site may be made up of amino acids from the alpha and/or beta chains of Mac-1.

A $D_{30}$ homolog is capable of inhibiting $D_{30}$ binding to the Mac-1 $D_{30}$ binding site if the $D_{30}$ homolog competes with or blocks the binding of $D_{30}$ to the Mac-1$D_{30}$ binding site. Methods and procedures for determining inhibition are well known in the art and include the use of competition assays similar to the antigen competition assays described in *Antibodies: A Laboratory Manual*, Harlow and Lane, eds., Cold Spring Harbor, N.Y. (1988). For example, an unlabelled compound suspected of being a $D_{30}$ homolog can be used to inhibit the binding of labelled $D_{30}$ or a labelled $D_{30}$ homolog to the Mac-1 $D_{30}$ binding site of the Mac-1 receptors on leukocytes. The amount of labelled $D_{30}$ binding to the $D_{30}$ binding site in the presence or absence of the unlabelled compound would be compared and if the presence of the unlabelled compound inhibits amount of labelled $D_{30}$ binding to the $D_{30}$ binding site, then the unlabelled compound is a $D_{30}$ homolog. A preferred method for measuring inhibition of $D_{30}$ binding to Mac-1 is described in Example 2.

A $D_{30}$ homolog of the present invention may be a portion of either fibrinogen or $D_{30}$ so long as that particular portion is capable of inhibiting $D_{30}$ binding to the Mac-1 $D_{30}$ binding site. Proteins or polypeptides that are homologous to all or a portion of $D_{30}$ or homologous to all or a portion of fibrinogen are also contemplated as $D_{30}$ homologs. These homologous proteins are capable of inhibiting $D_{30}$ binding to the Mac-1 $D_{30}$ binding site and therefore are true $D_{30}$ homologs.

$D_{30}$ homologs containing non-natural amino acids and/or amino acids with non-natural side groups are also contemplated. Examples of non-natural amino acids include amino acids having chemically derivatized side groups, or ornithine or citrulline. Examples of amino acids with non-natural side groups include amide residues necessary to cyclize the peptide.

A $D_{30}$ homolog of the present invention may be coupled to or conjugated with another protein or polypeptide to produce a $D_{30}$ homolog conjugate. A $D_{30}$ homolog conjugate has advantages over a $D_{30}$ homolog used alone. For example, coupling the $D_{30}$ homolog to a protein or polypeptide known to contain a second biological function allows the targeting of that second biological function to the location at or near a Mac-1 receptor or Mac-1 $D_{30}$ binding site.

When coupled to a carrier to form what is known in the art as a carrier-hapten conjugate, a $D_{30}$ homolog of the present invention is capable of inducing antibodies that immunoreact with a $D_{30}$ homolog. In view of the well established principle of immunologic cross-reactivity, the present invention therefore contemplates antigenically related variants of a $D_{30}$ polypeptide. An "antigenically related variant" is a subject polypeptide that is capable of inducing antibody molecules that immunoreact with a $D_{30}$ polypeptide of this invention and with $D_{30}$.

Any peptide of the present invention may be used in the form of a pharmaceutically acceptable salt. Suitable acids which are capable of forming salts with the peptides of the present invention include inorganic acids such as hydrochloric acid, hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Suitable bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g. triethylamine, diisopropyl amine, methyl amine, dimethyl amine and the like) and optionally substituted ethanolamines (e.g. ethanolamine, diethanolamine and the like).

In other preferred embodiments a $D_{30}$ homolog is conjugated with a carrier molecule to form a $D_{30}$ homolog conjugate containing at least one carrier molecule. Typical carriers include sepharose, sephadex, proteins, polypeptides and the like.

A $D_{30}$ homolog may also be conjugated to itself or aggregated in such a way as to produce a large complex containing a $D_{30}$ homolog. A large complex containing a $D_{30}$ homolog is advantageous because it has new biologic properties such as longer half-life in circulation or greater activity.

C. Compositions Containing $D_{30}$ Homologs

In one preferred embodiment, the invention contemplates a composition comprising a carrier and a therapeutically effective amount of a substantially pure and pharmaceutically acceptable $D_{30}$ homolog capable of binding to the Mac-1 $D_{30}$ binding site and inhibiting fibrinogen binding to the Mac-1 $D_{30}$ binding site.

A therapeutically effective amount of a $D_{30}$ homolog is an amount that when administered to a patient is capable of inhibiting fibrinogen binding to the Mac-1 $D_{30}$ binding site. Assays for detecting the inhibition of fibrinogen binding to the Mac-1 $D_{30}$ binding site include, but are not limited to the competitive and other binding assays described in Section E or Example 2 of this specification. Preferably, a therapeutically effective amount of a $D_{30}$ homolog is an amount that reduces (inhibits) fibrinogen binding to Mac-1 by at least 10 percent, preferably by at least 50 percent, and more preferably by at least 99 percent, when measured in an in vitro assay for fibrinogen binding to Mac-1. An exemplary in vitro assay to quantitate effective inhibitory amounts of $D_{30}$ homolog is described in Example 2. In preferred methods, a therapeutic composition is useful for inhibiting Mac-1 receptor-mediated inflammation in a patient exhibiting inflammation as described further herein. In this embodiment, a therapeutically effective amount is an amount that when administered to a patient is sufficient to inhibiting Mac-1 receptor-mediated inflammation.

Assays for detecting the inhibition of Mac-1 receptor-mediated inflammation include, but are not limited to the lymphocyte migration assays described in section E of this application. Additional means to detect inhibition of Mac-1 receptor-mediated inflammation include clinical inspection of symptoms attendant in a patient presenting with inflammation.

Substantially pure, when used in the context of a $D_{30}$ homolog, refers to compositions that are enriched in $D_{30}$ homolog, and preferably are free of detectable amounts of blood cells, immunoglobulin and albumin proteins, and lipoproteins, and more preferably contains in excess of 99 percent by weight of $D_{30}$ homolog per total mass in the composition.

By pharmaceutically acceptable is meant that a $D_{30}$ homolog, when used in a therapeutic composition, does not cause any undesirable physiological effects due to the presence of contaminants. Thus a pharmaceutically acceptable $D_{30}$ homolog is free of pharmaceutically unacceptable contaminants such as pyrogens (lipopolysaccharides) and other contaminants such as poisonous chemicals (i.e., sodium azide) and detergents, namely sodium dodecyl sulfate.

The preparation of therapeutic compositions which contain polypeptides or proteins as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is mixed with inorganic and/or organic carriers which are pharmaceutically acceptable and compatible with the active ingredient. Carriers are pharmaceutically acceptable excipients (vehicles) comprising more or less inert substances when added to a therapeutic composition to confer suitable consistency or form to the composition. Suitable carriers are, for example, water, saline, dextrose, glycerol, ethanol, or the like and combinations thereof. In addition, if desired, the composition can contain minor amounts of auxiliary substances such as wetting or emulsifying agents and pH buffering agents which enhance the effectiveness of the active ingredient.

A therapeutic composition useful in the practice of the present invention typically contains a $D_{30}$ homolog formulated into the therapeutic composition as a neutralized pharmaceutically acceptable salt form. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic $D_{30}$ homolog containing composition is conventionally administered parenterally, as by injection of a unit dose, for example. In this way the therapeutic composition can be delivered intravenously, intramuscularly or into other regions, such as into synovial fluids. However delivery of a $D_{30}$ homolog containing composition transdermally is also contemplated. The term "unit dose" when used in reference to a therapeutic composition used in the present invention refers to physically discrete units suitable as unitary dosages for humans, each unit containing a predetermined quantity of active material calculated to produce the desired therapeutic effect in association with the required diluent, carrier or excipient.

In preferred embodiments, a therapeutic composition of the present invention contains an effective amount of a $D_{30}$ homolog and is a sterile composition. A sterile composition is substantially free of bacteria and fungus. Typically a composition is made sterile by passing the composition through a filter such as a 0.2 micron filter designed for this purpose.

In other preferred embodiments, a composition of the present invention is optimized to allow the $D_{30}$ homolog it contains to be delivered transdermally.

In other preferred embodiments, a composition of the present invention contains an immunologically effective amount of $D_{30}$ homolog. An immunologically effective amount of $D_{30}$ homolog is an amount sufficient to produce antibodies that immunoreact with a $D_{30}$ homolog.

D. Antibodies and Monoclonal Antibodies

The term "antibody" in its various grammatical forms is used herein as a collective noun that refers to a population of immunoglobulin molecules and/or immunologically active portions of immunoglobulin molecules, i.e., molecules that contain an antibody combining site or paratope.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules for use in the diagnostic methods and systems of the present invention are intact immunoglobulin molecules, substantially intact immunoglobulin molecules and those portions of an immunoglobulin molecule that contain the paratope, including those portions known in the art as Fab, Fab', F(ab')$_2$ and F(v).

Fab and F(ab')$_2$ portions of antibodies are prepared by the proteolytic reaction of papain and pepsin, respectively, on substantially intact antibodies by methods that are well known. See for example, U.S. Pat. No. 4,342,566, Inbar et al., *Proc. Natl. Acad. Sci. USA*, 69:2659–62 (1972), and Goding, *Monoclonal Antibodies: Principles and Practice*, Academic Press, P118–124 (1983).

Fab' antibody portions are also well known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules are preferred, and are utilized as illustrative herein.

1. Anti-$D_{30}$ Idiotype Antibodies

In one embodiment, present invention contemplates methods and compositions employing an anti-($D_{30}$ idiotype) antibody.

Anti-idiotype antibodies are antibodies that have the internal image of a particular entity and therefore express antigenic determinants or epitopes that are immunochemically similar or identical to the epitopes found on an external antigen. For example, an anti-($D_{30}$ idiotype) antibody is an anti-idiotype antibody that contains the internal image of the portion of $D_{30}$ that binds to the Mac-1 receptor $D_{30}$ binding site.

An anti-($D_{30}$ idiotype) antibody contains a paratope whose structure is defined by the ability to:

(1) bind to the Mac-1 $D_{30}$ binding site to form a Mac-1 $D_{30}$ binding site/anti-($D_{30}$ idiotype) antibody complex, and (2) immunoreact with an anti-$D_{30}$ homolog antibody as defined herein.

An anti-($D_{30}$ idiotype) antibody binds to the Mac1$D_{30}$ binding site and forms Mac-1 $D_{30}$ binding site anti-($D_{30}$ idiotype) antibody complex if it competes with a $D_{30}$ homolog for binding to the Mac-1 $D_{30}$ binding site in a competition assay that, for example, employs a labelled $D_{30}$ homolog.

An anti-($D_{30}$ idiotype) antibody immunoreacts with an anti-$D_{30}$ homolog antibody. Various immunoassays for detecting the formed immunoreaction product or complex are well known and include radio-immunoassays and enzyme-linked immunoassays. See, for example, *Antibodies: A Laboratory Manual*, Harlow and Lane, eds., Cold Spring Harbor, N.Y. (1988).

An anti-($D_{30}$ idiotype) antibody of the present invention can be distinguished from anti-Mac-1 receptor antibodies that block $D_{30}$ binding to the Mac1 receptor because anti-($D_{30}$ idiotype) antibodies immunoreact with anti-$D_{30}$ antibodies and anti-Mac-1 receptor antibodies do not.

An anti-($D_{30}$ idiotype) antibody is prepared using methods and procedures well known in the art. See, for example, Benjamini et al., Immunogens and Improved Methods of Making Immunogens, International Publication No. WO 88/00472, published Jan. 28, 1988; Standt et al., *J. Exp. Med.*, 157:687–704 (1983); Reagan et al., *J. Virol.*, 48:660–666 (1983), and Ardman et al., *J. Exp. Med.*, 161:669–686 (1985). Briefly, to produce an anti-($D_{30}$ idiotype) antibody composition of this invention, an anti-$D_{30}$ homolog antibody is first produced by inoculating a laboratory animal with an immunologically effective amount of a $D_{30}$ homolog, typically present in a vaccine to produce an anti-$D_{30}$ homolog antibody.

Methods for producing anti-$D_{30}$ homolog antibodies for use in the production of anti-($D_{30}$ idiotype) antibodies are well known. See for example, *Antibodies: A Laboratory Manual*, Harlow and Lane, eds., Cold Spring Harbor, N.Y. (1988) for a description of the process of producing polyclonal or preferably monoclonal antibodies against a protein such as a $D_{30}$ homolog.

A vaccine useful for preparing anti-idiotype antibodies of the present invention comprises immunologically effective amounts of both a $D_{30}$ homolog and an immunopotentiator suitable for use in mammals.

An immunopotentiator is a molecular entity that stimulates maturation, differentiation and function of B and/or T lymphocytes. Immunopotentiators are well known in the art and include T cell stimulating polypeptides such as those described in U.S. Pat. No. 4,426,324 and the C8-substituted guanine nucleosides described by Goodman et al., *J. Immunol.*, 135:3284–88 (1985) and U.S. Pat. No. 4,643,992.

The phrases "suitable for use in mammals" and "pharmaceutically acceptable" refer to molecular entities and compositions that do not produce an allergic or similar untoward reaction when administered to a mammal.

A vaccine can also include an adjuvant as part of the excipient. Adjuvants such as complete Freund's adjuvant (CFA) and incomplete Freund's adjuvant (IFA) for use in laboratory mammals are well known in the art. Pharmaceutically acceptable adjuvants such as alum can also be used. An exemplary vaccine thus comprises one ml of phosphate buffered saline (PBS) containing about 1 mg to about 5 mg $D_{30}$ homolog adsorbed onto about 0.5 mg to about 2.5 mg of alum. A preferred vaccine comprises 1 ml of PBS containing 1 mg $D_{30}$ homolog adsorbed onto 2.5 mg of alum.

The anti-$D_{30}$ homolog antibodies produced by the above vaccination are collected from the mammal and those immunospecific for the $D_{30}$ homolog are isolated to the extent desired by well known techniques such as, for example, immunoaffinity chromatography.

Monoclonal anti-$D_{30}$ homolog antibody compositions may also be produced using methods well known in the art. See, for example, *Antibodies: A Laboratory Manual*, Harlow and Lane, eds., Cold Spring Harbor, N.Y. A monoclonal anti-$D_{30}$ homolog antibody contains, within detectable limits, only one species of antibody combining site capable of effectively immunologically binding a $D_{30}$ homolog and displays a single binding affinity for a $D_{30}$ homolog.

The monoclonal or polyclonal anti-D30 homolog antibody produced above is used to prepare an anti-($D_{30}$ idiotype) antibody by inoculating a laboratory mammal with an effective amount of the anti-$D_{30}$ homolog antibody produced above to produce anti-($D_{30}$ idiotype) antibodies. The anti-($D_{30}$ idiotype) antibodies capable of binding an anti-$D_{30}$ homolog antibody are isolated, to the extent desired by well known techniques such as, for example, immunoaffinity chromatography.

Anti-($D_{30}$ idiotype) antibodies capable of binding an anti-$D_{30}$ homolog antibody are then assayed for their ability to bind to the Mac-1 $D_{30}$ binding site indicating that these anti-idiotype antibodies have the internal image of a $D_{30}$ homolog. Anti-($D_{30}$ idiotype) antibodies that bind the Mac-1 $D_{30}$ binding site are selected and are useful in practicing this invention. Typically, an anti-($D_{30}$ idiotype) antibody is assayed for its ability to bind to Mac-1 $D_{30}$ binding site by a competition assay with a labelled $D_{30}$ homolog. An anti-($D_{30}$ idiotype) antibody that competes in this competition assay is then selected.

Suitable anti-($D_{30}$ idiotype) antibodies in monoclonal form, typically whole antibodies, can also be prepared using hybridoma technology described by Reagan et al., *Proc. Natl. Acad. Sci., USA*, 84:3891–95 (1987), which description is incorporated herein by reference. Briefly, to form the hybridoma from which the monoclonal anti-idiotypic antibody composition is produced, a myeloma or other self-perpetuating cell line is fused with lymphocytes obtained from the spleen of a mammal hyperimmunized with an anti-$D_{30}$ homolog antibody.

It is preferred that the myeloma cell line be from the same species as the lymphocytes. Typically, a mouse of the strain 129 GlX⁺ is the preferred mammal. Suitable mouse myelomas for use in the present invention include the hypoxanthine-aminopterin-thymidine-sensitive (HAT) cell lines P3X63-Ag8,653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas secreting the anti-idiotypic antibody molecules of this invention are identified using serological methods such as a commercially available enzyme linked immunosorbent assay (ELISA) diagnostic assay for detecting antibodies to an anti-$D_{30}$ homolog antibody. Once the hybridoma is shown to be secreting an anti-idiotypic antibody that binds an anti-$D_{30}$ homolog antibody, these antibodies are further screened for their ability to compete with a $D_{30}$ homolog for binding to the Mac-1 $D_{30}$ binding site.

A monoclonal anti-idiotypic antibody composition of the present invention can be produced by initiating a monoclonal hybridoma culture comprising a nutrient medium containing a hybridoma that secretes antibody molecules of the appropriate anti-($D_{30}$ idiotype) specificity. The culture is maintained under conditions and for a time period sufficient for the hybridoma to secrete the antibody molecules into the medium. The antibody-containing medium is then collected. The anti-($D_{30}$ idiotype) antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., *Virol.*, 8:396 (1959)) supplemented with 4.5 gm/l glucose, 20 mm glutamine, and 20% fetal calf serum. An exemplary inbred mouse strain is the Balb/c.

2. Anti-$D_{30}$ Receptor Binding Site Specific Antibodies

In another embodiment, the present invention contemplates an antibody having antibody molecules that immunoreact with $D_{30}$ at the Mac-1 receptor binding site. Stated differently, the antibody is specific for the receptor binding site on $D_{30}$ as defined herein, and is referred to as an anti-$D_{30}$ receptor binding site specific antibody.

An anti-$D_{30}$ receptor binding site specific antibody is capable of immunologically binding with a $D_{30}$ fragment of fibrinogen but does not bind other fragments of fibrinogen, including such other fragments as the N-terminus of the α chain up to amino acid 130, the N-terminus of the β chain up to amino acid 130, or the extreme C-terminus of the gamma chain. The $D_{30}$ receptor binding site specific antibody binds the Mac-1 $D_{30}$ binding site present on $D_{30}$ and thus inhibits $D_{30}$ homolog binding to Mac-1 receptor via the Mac-1 $D_{30}$ binding site.

The Mac-1 $D_{30}$ binding site is that portion of $D_{30}$ that is bound by the Mac-1 receptor. Fragments derived from or homologous to $D_{30}$ may contain a Mac-1 $D_{30}$ binding site.

In preferred embodiments an, an anti-$D_{30}$ receptor binding site specific antibody of this invention comprises antibody molecules that immunoreact with:

(a) $D_{30}$, and (b) a $D_{30}$ polypeptide of this invention; but is substantially free from immunoreaction with the polypeptide having an amino acid residue sequence represented by the formula: GLYFIKPLKANQQFLVYCEIDGSGC (10:169–188). Preferably, the anti-$D_{30}$ receptor binding site specific antibody does not immunoreact with one or more of the polypeptides shown in Table 1 and designated DI, DII, DIV, G1, G2, G3, G4, G5, G6, G9 or G11.

By "substantially free" means that the antibody molecules do not immunoreact with the stated antigen at levels within one order of magnitude, and preferably within two orders of magnitude, of the level of immunoreaction with a species of antigen recited to immunoreact with the antibody molecule when immunoreaction is expressed as an equilibrium constant between bound (immunoreacted) and nonbound antigen.

In preferred embodiments, an anti-$D_{30}$ receptor binding site specific antibody is characterized as being capable of immunoreacting with a polypeptide having an amino acid residue sequence represented by a formula selected from the group consisting of:

QKRLDGSVDFKK, (3:195–206)

GQKRLDGSVDFKK, (11:195–206)

WTVFQKRLDGSV, (3:191–202)

GQKRLDGS, (11:195–201)

KYGWTVFQKRLDGSV, and (12:191–202)

KYGQKRLDGS. (13:195–201)

Antibody reactivity with a $D_{30}$ polypeptide can be measured by a variety of immunological assays known in the art. Exemplary immunoreaction assays are described herein.

The production of both polyclonal and monoclonal antibodies against polypeptides and proteins are well known in the art. For example, see Example 3 of this application and *Antibodies: A Laboratory Manual*, Harlowe and Lane, Eds., Cold Spring Harbor, N.Y. (1988).

An anti-$D_{30}$ receptor binding site specific antibody of the present invention is typically produced by immunizing a mammal with an inoculum containing a $D_{30}$ polypeptide of this invention and thereby induce in the mammal antibody molecules having immunospecificity for the immunizing polypeptide. The antibody molecules are then collected from the mammal and isolated to the extent desired by well known techniques such as, for example, by using DEAE Sephadex to obtain the IgG fraction. Exemplary antibody preparation methods using $D_{30}$ polypeptides in the immunogen are described herein.

The preparation of antibodies against polypeptide is well known in the art. [See Staudt et al., *J. Exp. Med.*, 157:687–704 (1983)]. Briefly, to produce a peptide antibody composition of this invention, a laboratory mammal is inoculated with an immunologically effective amount of a $D_{30}$ polypeptide, typically as present in a vaccine of the present invention. The anti-$D_{30}$ polypeptide antibody molecules thereby induced are then collected from the mammal and are isolated to the extent desired by well known techniques such as, for example, by immunoaffinity chromatography.

To enhance the specificity of the antibody, the antibodies are preferably purified by immunoaffinity chromatography using solid phase-affixed immunizing polypeptide. The antibody is contacted with the solid phase-affixed immunizing polypeptide for a period of time sufficient for the polypeptide to immunoreact with the antibody molecules to form a solid phase-affixed immunocomplex. The bound antibodies are separated from the complex by standard techniques.

The word "inoculum" in its various grammatical forms is used herein to describe a composition containing a $D_{30}$ polypeptide or $D_{30}$ homolog of this invention as an active ingredient used for the preparation of antibodies of this invention. When a polypeptide is used in an inoculum to induce antibodies it is to be understood that the polypeptide can be used in various embodiments, e.g., alone or linked to a carrier as a conjugate, or as a polypeptide polymer. However, for ease of expression and in context of a polypeptide inoculum, the various embodiments of the polypeptides of this invention are collectively referred to herein by the term "polypeptide" and its various grammatical forms.

For a polypeptide that contains fewer than about 35 amino acid residues, it is preferable to use the peptide bound to a carrier for the purpose of inducing the production of antibodies.

One or more additional amino acid residues can be added to the amino- or carboxy-termini of the polypeptide to assist in binding the polypeptide to a carrier. Cysteine residues added at the amino- or carboxy-termini of the polypeptide have been found to be particularly useful for forming conjugates via disulfide bonds. However, other methods well known in the art for preparing conjugates can also be used.

The techniques of polypeptide conjugation or coupling through activated functional groups presently known in the art are particularly applicable. See, for example, Aurameas, et al., *Scand. J. Immunol.*, Vol. 8, Suppl. 7:7–23 (1978) and U.S. Pat. No. 4,493,795, No. 3,791,932 and No. 3,839,153. In addition, a site directed coupling reaction can be carried out so that any loss of activity due to polypeptide orientation after coupling can be minimized. See, for example, Rodwell et al., *Biotech.*, 3:889–894 (1985), and U.S. Pat. No. 4,671,958.

Exemplary additional linking procedures include the use of Michael addition reaction products, dialdehydes such as glutaraldehyde, Klipstein, et al., *J. Infect. Dis.*, 147:318–326 (1983) and the like, or the use of carbodiimide technology as in the use of a water-soluble carbodiimide to form amide links to the carrier. Alternatively, the heterobifunctional crosslinker SPDP (N-succinimidyl-3-(2-pyridyldithio) propionate)) can be used to conjugate peptides, in which a carboxy-terminal cysteine has been introduced.

Useful carriers are well known in the art, and are generally proteins themselves. Exemplary of such carriers are keyhole limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular animal to be inoculated should be selected.

The present inoculum contains an effective, immunogenic amount of a polypeptide of this invention, typically as a conjugate linked to a carrier. The effective amount of polypeptide per unit dose sufficient to induce an immune response to the immunizing polypeptide depends, among other things, on the species of animal inoculated, the body weight of the animal and the chosen inoculation regimen as is well known in the art. Inocula typically contain polypeptide concentrations of about 10 micrograms to about 500 milligrams per inoculation (dose), preferably about 50 micrograms to about 50 milligrams per dose.

The term "unit dose" as it pertains to the inocula refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals, as disclosed in detail herein, these being features of the present invention.

Inocula are typically prepared from the dried solid polypeptide-conjugate by dispersing the polypeptide-conjugate in a physiologically tolerable (acceptable) diluent such as water, saline or phosphate-buffered saline to form an aqueous composition.

Inocula can also include an adjuvant as part of the diluent. Adjuvants such as complete Freund's adjuvant (CFA), incomplete Freund's adjuvant (IFA) and alum are materials well known in the art, and are available commercially from several sources.

The anti-$D_{30}$ receptor binding site specific antibody so produced can be used, inter alia, in the diagnostic methods and systems of the present invention to detect $D_{30}$ homologs present in a sample such as a body fluid sample. In addition the anti-$D_{30}$ receptor binding site specific antibody can be used in therapeutic methods for inhibiting Mac-1 binding to $D_{30}$ homologs based on the ability of the antibody to specifically bind the $D_{30}$ receptor binding site and block Mac-1 binding.

Monoclonal anti-$D_{30}$ receptor binding site specific antibodies are particularly preferred and can be produced as previously described using the $D_{30}$ polypeptides of this invention in the inoculum.

E. Methods of Inhibiting Mac-1 Receptor Binding To A Mac-1 Ligand and Inhibition of Mac-1 Receptor-Mediated Inflammation 1. Therapeutic Methods Using A $D_{30}$ Homolog The present invention contemplates a method of inhibiting Mac-1 receptor binding to a Mac-1 $D_{30}$ binding site ligand (Mac-1 ligand) in a patient by administering to the patient a therapeutically effective amount of a composition containing a $D_{30}$ homolog of this invention dispersed in a pharmaceutically acceptable excipient. Binding of Mac-1 receptor to a Mac-1 $D_{30}$ binding site ligand therefor forms a Mac-1 receptor:Mac-1 $D_{30}$ binding site ligand complex.

A Mac-1 ligand is any protein, virus, polypeptide, parasite, bacteria, hormone, effector molecule, cell-surface molecule, immune cell or portion thereof that binds to the $D_{30}$ binding site present on the Mac-1 receptor and inhibits the binding of $D_{30}$ to the Mac-1 $D_{30}$ binding site. Examples of Mac-1 $D_{30}$ binding site ligands include $D_{30}$, fibrinogen, and various bacterial parasites. See for example Payne et al., *J. Exp. Med.*, 166:329–331 (1987) and Russell et al., *J. Exp. Med.*, 168:279–292 (1988). In the description below, fibrinogen will be used as an exemplary Mac-1 $D_{30}$ binding site ligand and thus it should be understood that the invention contemplates all Mac-1 $D_{30}$ binding site ligands and is not limited to fibrinogen.

The inhibition of Mac-1 receptor-mediated fibrinogen binding in a patient is detected by assaying the patient's neutrophil function. These assays may be performed in vivo or in vitro and include assays to detect cell adherence, chemotaxis and phagocytosis and the inability to localize in vivo to sites of inflammation. See, for example, Tayler et al., *J. Clin. Invest.*, 67:584 (1984), and Price et al., *J. Immunol.*, 139:4174–4177 (1987).

The inhibition of Mac-1 receptor-mediated fibrinogen binding can be determined in vivo by determining the amount of $D_{30}$ homolog binding to neutrophils isolated from the patient. Blood samples are drawn at various times following administration of $D_{30}$ homolog and the amount of additional labelled fibrinogen or $D_{30}$ homolog that can be bound to the neutrophils isolated from the blood samples is determined. By comparing the amount of additional labelled fibrinogen or $D_{30}$ homolog that binds to these neutrophils to the amount of labelled fibrinogen or $D_{30}$ homolog bound by control lymphocytes, the level of inhibition of Mac-1 mediated fibrinogen binding is determined. See, for example, Price et al., *J. Immunol.*, 139:4174–4177 (1987).

Other methods of determining the inhibition of Mac-1 receptor-mediated fibrinogen binding include detection of neutrophil migration into inflammatory sites in vivo. Typically, inflammation sites can be created by placing polyvinyl sponges packed in formation at various subcutaneous sites. See for example Price et al., *J. Immunol.*, 139:4174–4177 (1987) and Price et al., *J. Clin. Invest.*, 59:475 (1977). The sponges are place subcutaneously by making sterile incisions. Blood samples are drawn directly from the subcutaneous sponges and the number of neutrophils determined. Blood samples are drawn at various times before and after administration of the $D_{30}$ homolog, the number of neutrophils determined and therefore the amount of Mac-1 receptor-mediated fibrinogen binding is determined.

Other methods of detecting a change in the pattern of neutrophil migration in vivo including various methods of detecting the location of neutrophils using labelled antibodies that bind neutrophils would also be useful in practicing this invention. One skilled in the art will understand that these techniques allow the localization of labeled cells within a live patient. For examples of various in vivo imaging techniques, see Zalcberg, *Am. J. Clin. Oncol.*, 8:481–484 (1985); Delaloye et al., *J. Clin . Invest.*, 37:301–311 (1986); Haber, *Ann. Rev. Med.*, 37:249–261 (1986); and Wahl et al., *J. Nucl. Med.*, 24:316–325 (1983).

Patients in which the inhibition of Mac-1 receptor binding to a Mac-1 ligand such as fibrinogen would be clinically useful include patients with very recent myocardial infarction (within 40 hours of the acute event) where the $D_{30}$ homolog would prevent neutrophil accumulation on exposed tissues due to injury to those tissues. Other patients needing inhibition of Mac-1 receptor binding to Mac-1 ligands include patients with autoimmune responses, general inflammatory or localized inflammatory reactions and patients with glomerular nephritis.

The present invention also contemplates a method of inhibiting Mac-1 receptor-mediated inflammation in a patient by administering to the patient a therapeutically effective amount of a composition comprising a substantially pure and pharmaceutically acceptable $D_{30}$ homolog dispersed together with a pharmaceutically acceptable excipient (carrier).

The inhibition of Mac-1 receptor-mediated inflammation is detected by the inhibition of neutrophil accumulation at the site of an inflammation producing injury or wound. For example, the number of neutrophils that accumulate at the site of a sponge placed under the skin can be determined both before and after a $D_{30}$ homolog is administered to the patient. See, for example, Price et al., *J. Immunol.*, 139:4174–4177 (1987).

Mac-1 receptor-mediated inflammation includes any of the various biological functions possessed by a lymphocyte having a Mac-1 receptor on its cell surface. Typical biological functions possessed by such lymphocytes include adhesion of Mac-1 bearing cells to vascular endothelium, phagocytosis of complement opsonized particles, chemotaxis and specific interactions with extracellular matrix proteins.

The present invention also contemplates the inhibition of other Mac-1 mediated lymphocyte functions that occur upon binding of a $D_{30}$ homolog to the Mac-1 receptor. Inhibition of this type of metabolic response is contemplated by the present invention. For example, upon neutrophil activation, metabolic events such as a burst of $O_2$ generation are known to occur. See Nathan et al., *J. Cell Biol.*, 109:1341–1349 (1989).

A $D_{30}$ homolog is typically administered as a pharmaceutically acceptable composition in the form of a solution or suspension, however, as is well known, peptides and proteins such as a $D_{30}$ homolog can also be formulated for therapeutic administration as tablets, pills, capsules, sustained release formulations or powders. In any case, the administered composition contains at least about 0.10% to about 99% by weight of a $D_{30}$ homolog per weight of composition, preferably 10% –90% and more preferably 25–75% .

The composition is administered in a manner compatible with the dosage formulation, and in a therapeutically effective amount. The quantity to be administered depends on the subject to be treated, capacity of the subject's blood hemostatic system to utilize the active ingredient, and degree of either Mac-1 receptor-mediated inflammation inhibition or Mac-1 receptor-mediated fibrinogen binding inhibition desired. Precise amounts of active ingredient required to be administered depend on the judgement of the practitioner and are peculiar to each individual.

A therapeutically effective amount of $D_{30}$ homolog can be expressed as an amount sufficient to produce a final concentration of $D_{30}$ homolog in a patient's blood. That blood concentration can be determined by an in vitro assay for $D_{30}$ in a liquid body sample (e.g., blood), such as is described herein, or can be calculated based on the patient's body weight and blood volume as is well known.

Suitable dosage ranges of a $D_{30}$ homolog in the form of $D_{30}$ or a $D_{30}$ polypeptide of this invention for the therapeutic methods described herein are in the order of 0.1 to 20 milligrams, preferably one to ten milligrams of $D_{30}$ homolog per kilogram of body weight of patient per day, and depending on the route of administration. Stated differently, a therapeutically effective dosage is an amount sufficient to produce an intravascular concentration of $D_{30}$ in the blood of the patient in the range of 0.1 to 100 micrograms/milliliter (μg/ml), preferably about 10 to 20 μg/ml.

The present invention also contemplates a method of inhibiting Mac-1 mediated fibrinogen binding in a patient comprising administering to said patient a therapeutically effective amount of an anti-($D_{30}$ idiotype) antibody which is detected by assaying the patients lymphocyte or neutrophil function. Assays to determine a patient's lymphocyte or neutrophil function are the same or similar assays to those used to determine lymphocyte function described above.

The inhibition of Mac-1 receptor-mediated fibrinogen binding can be determined in vivo by determining the amount of anti-($D_{30}$ idiotype) antibody binding to neutrophils isolated from the patient. Blood samples are drawn at various times following administration of the anti-($D_{30}$ idiotype) antibody and the amount of additional labelled fibrinogen or $D_{30}$ homolog that can be bound to the neutrophils isolated from the blood samples is determined. By comparing the amount of additional labelled fibrinogen or $D_{30}$ homolog that bind to these neutrophils to the amount of labelled fibrinogen or $D_{30}$ homolog bound by control lymphocytes, the level of inhibition of Mac-1 mediated fibrinogen binding is determined. See, for example, Price et al., *J. Immunol.*, 139:4174–4177 (1987).

Other methods of determining the inhibition of Mac-1 receptor-mediated fibrinogen binding include detection of neutrophil migration into inflammatory sites in vivo. Examples of such assays were described above.

Other methods of detecting a change in the pattern of neutrophil migration in vivo after administration of an anti-($D_{30}$ idiotype) antibody including various methods of detecting the location of neutrophils using labelled antibodies that bind neutrophils would also be useful in practicing this invention.

The present invention also contemplates a method of inhibiting Mac-1 receptor-mediated inflammation in a patient by administering to the patient a therapeutically effective amount of a composition containing an anti-($D_{30}$ idiotype) antibody dispersed in a pharmaceutically acceptable excipient.

The inhibition of Mac-1 receptor-mediated inflammation is detected by detecting the inhibition of neutrophil accumulation at the site of an inflammation-producing injury or wound.

In other preferred embodiments, a method of inhibiting Mac-1 receptor-mediated fibrinogen binding in a patient by administering to the patient a therapeutically effective amount of an anti-($D_{30}$ idiotype) antibody is contemplated.

The anti-($D_{30}$ idiotype) antibody administered in these embodiments is a purified anti-($D_{30}$ idiotype) antibody and may be a solid, a liquid or a paste.

Other preferred embodiments contemplate a method of inhibiting Mac-1 receptor-mediated inflammation in a patient by administering to the patient a therapeutically effective amount of an anti-($D_{30}$ idiotype) antibody.

An anti-($D_{30}$ idiotype) antibody is typically administered as a pharmaceutically acceptable composition in the form of a solution or suspension. However, as is well known, peptides and proteins such as an anti-($D_{30}$ idiotype) antibody can also be formulated for therapeutic administration as tablets, pills, capsules, sustained release formulations or powders. Typically, suitable dosage ranges for an antibody composition are of the order of one to hundreds of nanomoles of $D_{30}$ homolog per kilogram body weight per minute and depend on the route of administration. In any case, the administered composition contains about 0.10% to about 99% of an anti-($D_{30}$ idiotype) antibody, preferably 10%–90% and more preferably 25–75%.

2. Therapeutic Methods Using an Anti-$D_{30}$ Receptor Binding Site Specific Antibody The anti-$D_{30}$ receptor binding site specific antibody of this invention is useful in therapeutic methods for inhibiting Mac-1 receptor binding to a Mac-1 $D_{30}$ binding site ligand (Mac-1 ligand) in a patient by administering to the patient a therapeutically effective amount of a composition containing an anti-$D_{30}$ receptor binding site specific antibody of this invention dispersed in a pharmaceutically acceptable excipient.

Insofar as the anti-$D_{30}$ receptor binding site specific antibody inhibits Mac-1 binding to a $D_{30}$ homolog as described before for a $D_{30}$ homolog, the present antibody is also useful in the beforedescribed method for inhibiting Mac-1 receptor-mediated inflammation in a patient comprising administering to the patient a therapeutically effective amount of an anti-$D_{30}$ receptor binding site specific antibody.

Therapeutically effective amounts used in the present methods are determined in the same manner as described previously for the therapeutic methods using $D_{30}$ homologs. These amounts are typically the same amounts as described previously for the anti-($D_{30}$ idiotype) antibody compositions, and are typically administered in the previously described manners.

F. Methods of Detecting $D_{30}$ Homologs and Mac1: $D_{30}$ Homolog Complexes The present invention contemplates any method that results in detecting a $D_{30}$ homolog by producing a reaction product using a monoclonal antibody, polyclonal antibody, or Mac-1 receptors. Those skilled in the art will understand that there are numerous well known clinical diagnostic chemistry procedures that can be utilized to form and detect such reaction products. Thus, while exemplary assay methods are described herein, the invention is not so limited.

Various heterogeneous and homogeneous assay protocols can be employed, either competitive or noncompetitive for detecting the presence and preferably the amount of a $D_{30}$ homolog in a liquid composition.

A $D_{30}$ homolog may be detected in any sample such as a solid, liquid or body fluid sample. In preferred embodiments a $D_{30}$ homolog is detected in body fluid samples include blood, plasma, serum, mucous, sputum and the like.

A $D_{30}$ homolog may also be detected in vitro or in vivo in various tissues and organs. In preferred embodiments tissue slices or tissue sections may be assayed for the presence and location of a $D_{30}$ homolog. In other preferred embodiments organs may be assayed in vivo for the presence and to determine the location of a $D_{30}$ homolog.

Detection of the amount of $D_{30}$ homolog present in vitro or in vivo is useful because the amount of homolog present correlates with the amount of $D_{30}$ binding and inflammation present in the animal being analyzed.

Determination of the amount of $D_{30}$ homolog bound and the amount of inflammation present in the animal being analyzed allows the therapeutic administration of a $D_{30}$ homolog to a patient to be monitored to determine the clinical state of the patient.

In preferred embodiments the present invention contemplates a method of detecting the presence and preferably the amount, of a $D_{30}$ homolog in a liquid composition. The steps of this method include:

(1) admixing a first sample of activated cells having Mac-1 receptors with a predetermined amount of a liquid composition containing a $D_{30}$ homolog and a predetermined amount of a labelled $D_{30}$ homolog to form a competition reaction admixture;

(2) maintaining the reaction admixture formed in step (1) for a predetermined time period sufficient for the $D_{30}$ homolog present in the liquid composition to bind to the Mac-1 receptors and form a Mac-1 receptor:$D_{30}$ homolog complex and to allow the labelled $D_{30}$ homolog to bind the Mac-1 receptors and form a labelled Mac-1 receptor:$D_{30}$ homolog complex;

(3) assaying for the presence and/or amount of labelled Mac-1 receptor:$D_{30}$ homolog complex formed in step (2) thereby detecting the presence and/or amount of a $D_{30}$ homolog in the composition.

In other preferred embodiments, the assaying step (c) further comprises the steps of:

(i) admixing a second sample of activated cells having Mac-1 receptors with a predetermined amount of labelled $D_{30}$ homolog to form a binding admixture;

(ii) maintaining the binding admixture formed in step (i) for a predetermined time period to allow the labelled $D_{30}$ homolog to bind the Mac-1 receptors and form a labelled Mac-1 receptor:$D_{30}$ homolog complex;

(iii) determining the amount of labelled Mac-1 receptor:$D_{30}$ homolog complex formed in step (ii);

(iv) comparing the amount of labelled Mac-1 receptor:$D_{30}$ homolog complex determined in steps (2) and (iii) thereby detecting the amount of a $D_{30}$ homolog in the liquid composition.

A first sample of activated cells having Mac-1 receptor are admixed with a predetermined amount of a liquid composition containing a $D_{30}$ homolog and a predetermined amount of a labelled $D_{30}$ homolog to form a competition reaction admixture.

Activated cells having Mac-1 receptors on their cell surface are prepared by isolating polymorphonuclear neutrophils, other lymphocytes or leukocytes and activating them with a chemotactic peptide such as formyl-methionyl-leucyl-phenylalanine (fMLP). For examples of protocols producing activated cells having Mac-1 receptors on their cell surface see, Altieri et al., *J. Cell Biol.*, 107:1893–1900 (1988) and Altieri et al., *J. Clin. Invest.*, 78:968–76 (1986).

The activated Mac-1 receptor-containing cell can be a neutrophil, polymorphonuclear (PMN) cell, an established tissue culture cell or any other cell known to contain Mac-1 receptor. Preferred are PMN's isolated from a human donor and activated as described in Example 2.

A predetermined amount of a liquid composition containing a $D_{30}$ homolog is an amount of $D_{30}$ containing liquid composition that is useful and easily assayed. This predetermined amount of $D_{30}$ homolog containing liquid composition has been shown to be useful by performing a series of test assays with an amount of liquid composition containing a known concentration of $D_{30}$ homolog and is sufficient to allow the assay to be performed. Preferred amounts of a liquid composition are from about 1 microliter (µl) to about 1000 µl. Preferably, the liquid composition contains about 2.5 millimolar calcium chloride.

The liquid composition also contains a labelled $D_{30}$ homolog. A label is an atom or molecule that is either directly or indirectly involved in the production of a detectable signal to indicate the presence of a complex. Any label or indicating means can be linked to or incorporated in an expressed protein, polypeptide, or antibody or monoclonal antibody composition of the present invention, or used separately, and those atoms or molecules can be used alone or in conjunction with additional reagents. Labels include various in vivo labels useful within the body of a patient such as $^{111}$In, $^{99}$Tc, $^{67}$Ga, $^{186}$Re, and $^{132}$I.

The label can be a fluorescent labelling agent that chemically binds to antibodies or antigens without denaturing them to form a fluorescent (dye) that is a useful immunofluorescent tracer. Suitable fluorescent labelling agents are fluorochromes such as fluorescein isocyanate (FIC), fluorescein isothiocyanate (FITC), 5-dimenthylamin-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques in found in Deluca, "Immunofluorescence Analysis", in *Antibody As A Tool*, Marchalonis et al., eds., John Wiley & Sons, Ltd., pp. 189–231 (1982), which is incorporated herein by reference.

In preferred embodiments the label is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-4-2-benzthiazoline-G-sulfonic acid) (ABTS).

Radioactive elements are also useful as labels. An exemplary radiolabel is a radioactive element that produces gamma ray emissions. Elements which themselves emit gamma rays, such as $^{124}$I, $^{125}$I, $^{128}$I, $^{131}$I, $^{132}$I, and $^{51}$Cr represent one class of gamma ray emission-producing radioactive element indicating groups. Particularly preferred is $^{125}$I. Another group of useful indicating groups are those elements such as $^{11}$C, $^{18}$F, $^{15}$O and $^{13}$N which themselves emit positrons. The positrons so emitted produce gamma rays upon encounters with electrons present in the animal's body. Also useful is a beta emitter, such as indium.

The linking of labels, i.e., labelling of, polypeptides and proteins such as a $D_{30}$ homolog is well known in the art. For instance, antibody molecules produced by a hybridoma can be labelled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8, 7:7–23 (1978), Rodwell et al., *Biotech.*, 3:889–894 (1985), and U.S. Pat. No. 4,493,795, which is incorporated herein by reference. In addition, site directed coupling reactions can be carried out so that the label does not substantially interfere with the ability of the antibody molecules to bind their specific antigen. See, for example, Rodwell et al., *Biotech.*, 3:889–894 (1985).

The reaction admixture is maintained for a predetermined time period sufficient for the $D_{30}$ homolog and the labelled $D_{30}$ homolog present in the liquid composition to bind to the Mac-1 receptors and form a Mac-1 receptor:$D_{30}$ homolog complex and a labelled Mac-1 receptor:$D_{30}$ homolog complex.

The amount of time sufficient for the $D_{30}$ homolog and the labelled $D_{30}$ homolog to bind the Mac-1 receptors depends upon several physical parameters including temperature and the concentration of the various reactants. In preferred embodiments, the predetermined time period is from about 1 minute to 24 hours. In more preferred embodiments the predetermined time period is from about 10 minutes to about 1 hour. In the most preferred embodiments, the predetermined time period is from about 15 minutes to 30 minutes. Typically this time period is predetermined to optimize the assay.

Typically the reaction admixture is maintained under biological assay conditions that maintain the activity of the polypeptide and protein molecules including the $D_{30}$ homolog and the Mac-1 receptor sought to be assayed, and include a temperature range of about 4 degrees C. (4° C.) to about 45° C., a pH value range of about 5 to about 9 and an ionic strength varying from that of distilled water to that of about one molar sodium chloride. Methods for optimizing such conditions are well know in the art.

The presence of labelled Mac-1 receptor:$D_{30}$ homolog complex formed by maintaining the reaction admixture in step (2) is assayed.

The direct or indirect methods used to assay for the presence of and preferably the amount of labelled Mac-1 receptor:$D_{30}$ complex formed depend on the particular label used and are well known in the art. For example, the amount of radioactivity in the labelled Mac-1 receptor:$D_{30}$ complex may be determined.

Alternatively, homogeneous assay methods such as those described in U.S. Pat. No. 4,536,479; 4,233,401; 4,233,402 and 3,996,345, whose disclosures are incorporated herein by reference, can be used to determine the amount of labelled Mac-1 receptor:$D_{30}$ complex formed in step (2).

In other preferred embodiments, the assaying step (3) is a competition assay. In these preferred embodiments a second sample of activated cells having Mac-1 receptors are admixed with a predetermined amount of labelled $D_{30}$ homolog to form a binding admixture.

Preferably, the second sample containing the same number of activated cells at the same concentration is admixed with the labelled $D_{30}$ homolog in this step as were admixed with the labelled and unlabelled $D_{30}$ homolog in step (1). The use of the same number of activated cells in step (1) and this step allows the easy comparison of the amount of labelled Mac-1 receptor:$D_{30}$ homolog complex formed in each step. Preferably, about $4\times10^6$ activated cells at a concentration of $1.5\times10^7$ activated cells per milliliter (ml) are admixed with the labelled $D_{30}$ homolog of this step.

The binding admixture formed in step (i) is maintained for a predetermined time period to allow the labelled $D_{30}$ homolog to bind the Mac-1 receptors and form a labelled Mac-1 receptor:$D_{30}$ homolog complex.

Preferably, the binding admixture formed in step (i) is maintained for the same predetermined time period and under the same biological assay conditions as the competition reaction admixture is in step (2). Maintaining the binding admixture and the competition reaction admixture for the same predetermined time period and under the same biological assay condition allows the amounts of labelled Mac-1 receptor:$D_{30}$ homolog complex determined in step (3) and step (iii) to be easily compared.

The amount of labelled Mac-1 receptor:$D_{30}$ homolog complex formed in step (ii) is determined.

Preferably, the method used to determine the amount of labelled Mac-1 receptor:$D_{30}$ homolog complex formed in step (ii) is the same method used to determine the amount of labelled Mac-1 receptor:$D_{30}$ homolog in step (3). By using the same determination method in both step (3) and this step, the amounts of labelled Mac-1 receptor:$D_{30}$ homolog complex formed in each step may be easily compared.

The amount of labelled Mac-1 receptor:$D_{30}$ homolog complex determined in step (3) and step (iii) are compared, thereby detecting the presence of a $D_{30}$ homolog in the liquid composition.

The amount of labelled Mac-1 receptor:$D_{30}$ homolog complex determined in step (iii) is used to determine the control value of labelled complex formed in the presence of no $D_{30}$ homolog. This control value is then subtracted from the amount of labelled Mac-1 receptor:$D_{30}$ homolog complex formed in step (iii).

If the amount of labelled Mac-1 receptor:$D_{30}$ homolog complex determined in step (iii) is greater than the amount of labelled Mac-1 receptor:$D_{30}$ homolog complex determined in step (3) then the liquid composition contains a $D_{30}$ homolog.

In preferred embodiments, the amount of $D_{30}$ homolog present in the liquid composition required to produce a given reduction in the amount of labelled Mac-1 receptor:$D_{30}$ homolog complex in step (3) has been predetermined. Typically, the reduction in labelled Mac-1 receptor:$D_{30}$ homolog complex produced by a series of liquid compositions containing known varied amounts of a $D_{30}$ homolog has been predetermined and used to produce standard curve.

In other preferred embodiments, the present invention contemplates another method of detecting the amount of a $D_{30}$ homolog in a liquid sample. The steps of this method include;

(1) admixing an anti-$D_{30}$ receptor binding site specific antibody with a predetermined amount of a liquid sample containing a $D_{30}$ homolog to form an immunoreaction admixture;

(2) maintaining the immunoreaction admixture formed in step (1) for a preselected time period sufficient for the $D_{30}$ homolog present in the liquid sample to bind to the antibody and form an immunoreaction complex containing $D_{30}$ homolog and anti-$D_{30}$ receptor binding site specific antibody; and (3) determining the amount of the immunoreaction complex formed in step (2), thereby detecting the amount of a $D_{30}$ homolog within the liquid sample.

A $D_{30}$ receptor binding site specific antibody of this invention (an anti-$D_{30}$ receptor binding site specific antibody immunospecific for the Mac-1 binding site on $D_{30}$ as defined herein) is admixed with a predetermined amount of a liquid sample containing a $D_{30}$ homolog to form an immunoreaction admixture.

In preferred embodiments, the anti-D30 receptor binding site specific antibody is a monoclonal antibody produced by a hybridoma or by various genetic engineering methods. See for example, Huse et al., *Science*, 246:1275 (1989).

Preferably, the liquid sample containing a $D_{30}$ homolog is a biological fluid sample such as blood, plasma, serum, sputum, saliva, and the like. Preferably, the amount of liquid sample admixed is known.

Preferably, the anti-$D_{30}$ receptor binding site specific antibody is labelled, i.e., operatively linked to an indicating means such as an enzyme, radionuclide and the like.

Preferably, the anti-$D_{30}$ receptor binding site specific antibody is present as part of the solid support, i.e., operatively linked to a solid matrix, so that the immunoreaction admixture formed is a solid and the amount of anti-$D_{30}$ receptor binding site specific antibody present in the immunoreaction admixture contains an excess of antibody combining sites relative to the amount of $D_{30}$ homolog present in the liquid sample.

The immunoreaction admixture is maintained for a predetermined time period sufficient for the $D_{30}$ homolog present in the liquid sample to bind to the antibody and form an immunoreaction complex containing a $D_{30}$ homolog and an anti-$D_{30}$ receptor binding site specific antibody.

Typically, the immunoreaction admixture is maintained under biological assay conditions for a time period such as about 10 minutes to about 20 hours at a temperature of about 4° C. to about 45° C., such time being sufficient for the $D_{30}$ homolog present in the liquid sample to immunoreact with (immunologically bind) a portion of the anti-$D_{30}$ receptor binding site specific antibody combining sites present in the anti-$D_{30}$ receptor binding site specific antibody to form a $D_{30}$ homolog containing immunoreaction product.

Biological assay conditions are those conditions that maintain the biological activity of the immunochemical reagents of this invention and the $D_{30}$ homolog site to be assayed. Biological assay conditions include a temperature of about 4° C. to about 45° C., a reagent value range of about 5 to about 9 and an ionic strength varying from that of distilled water to that of about 1 molar sodium chloride. Methods for optimizing such conditions are well known in the art.

The amount of the $D_{30}$ containing immunoreaction complex formed in step (2) is determined, thereby detecting the presence of a $D_{30}$ homolog within the liquid sample.

Determining the amount of the $D_{30}$ homolog containing immunoreaction product, either directly or indirectly, can be accomplished using assay techniques well known in the art, and typically depend upon the type of indicating means used.

In preferred competitive assay methods, the amount of product determined in step (3) is related to the amount of immunoreaction product similarly formed and determined using a control liquid sample in place of the liquid sample, wherein the control liquid sample contains a known amount of a $D_{30}$ homolog.

The present invention also contemplates a method of detecting the amount of a Mac-1 receptor:$D_{30}$ homolog complex in a liquid composition. This method comprises the steps of:

(1) admixing an anti-(Mac-1:$D_{30}$ homolog complex) antibody capable of specifically binding a Mac-1:$D_{30}$ homolog complex with a predetermined amount of a liquid sample containing a Mac-1 receptor:$D_{30}$ homolog complex antibody to form a immunoreaction admixture;

(2) maintaining the immunoreaction admixture for a predetermined time period sufficient for the Mac-1 receptor:$D_{30}$ homolog complex present in the liquid sample to bind to the antibody and form an immunoreaction complex containing the Mac-1 receptor:$D_{30}$ homolog complex and anti-(Mac-1:$D_{30}$ homolog complex) antibody; and (3) determining the amount of the immunoreaction complex formed, thereby detecting the presence of a Mac-1 receptor:$D_{30}$ homolog complex within the liquid sample.

Detection of the amount or presence of Mac-1 receptor:$D_{30}$ homolog complex in a liquid sample or composition obtained from an animal is useful because the amount of Mac-1 receptor:$D_{30}$ homolog complex present correlates with the amount of Mac-1 receptor bound to $D_{30}$ homolog and the amount of Mac-1 receptor-mediated inflammation present in that animal.

Determination of the amount of inflammation present or the amount of Mac-1 receptor bound by a $D_{30}$ homolog is important in monitoring the clinical state of a patient being treated with a $D_{30}$ homolog of other immunomodulating compounds.

Preferably, the liquid sample is a known amount of a body fluid such as blood or a blood derived product such as serum or plasma.

Preferably, the amount of anti-(Mac-1:$D_{30}$ homolog complex) antibody is known and contains an excess amount of antibody combining sites immunospecific for a Mac-1:$D_{30}$ homolog complex. An antibody immunospecific for a Mac-1:$D_{30}$ homolog complex immunoreacts with the complex but not Mac-1 or a $D_{30}$ homolog alone. Production of antibodies immunospecific for a complex and not the individual components of a complex are known. For example, see Example 7. Further preferred are embodiments where the anti-(Mac-1:$D_{30}$ homolog complex) antibody is labelled, i.e., operatively linked to an indicating means such as an enzyme, radionuclide and the like.

Preferably, the anti-(Mac-1:$D_{30}$ homolog complex) antibody is present as part of a solid support, i.e., operatively linked to a solid matrix, so that the immunoreaction admixture formed is a solid and a liquid phase.

The immunoreaction admixture is maintained for a predetermined time period sufficient for the Mac-1 receptor:$D_{30}$ homolog complex present in the liquid sample to bind the antibody and form an immunoreaction complex containing the Mac-1 receptor:$D_{30}$ homolog complex and the anti-(Mac-1:$D_{30}$ homolog complex) antibody.

Preferably, the immunoreaction is maintained under biological assay conditions for a predetermined time period such as about 10 minutes to about 20 hours at a temperature of about 4° C. to about 45° C., such time being sufficient for the Mac-1 receptor:$D_{30}$ homolog complex present in the liquid composition to immunoreact with (immunologically bind) a portion of the anti-(Mac-1:$D_{30}$ homolog complex) antibody combining in the antibody to form a Mac-1:$D_{30}$ homolog complex containing immunoreaction product.

Biological assay conditions are those that maintain the biological activity of the immunochemical reagents of this invention and the Mac-1 receptor:$D_{30}$ homolog complex sought to be assayed. Those conditions include a temperature of about 4° C. to about 45° C., a pH value range of about 5 to about 9 in an ionic strength varying from that of distilled water to about 1 molar sodium chloride. Methods for optimizing such conditions are well known in the art. The amount of the immunoreaction complex containing the Mac-1 receptor:$D_{30}$ homolog complex is detected, thereby detecting the presence of a Mac-1 receptor:$D_{30}$ homolog complex within the liquid sample.

Determining the amount of the Mac-1 receptor:$D_{30}$ homolog complex containing immunoreaction product formed, either directly or indirectly, can be accomplished by assay techniques well known in the art, and typically depend on the type of indicating means used.

G. Detection of Mac-1 Receptors In Vivo

A method of detecting the presence and preferably the amount and location of cells having Mac-1 receptors in a mammal is contemplated. An effective amount of a composition containing a physiologically tolerable diluent and an amount of $D_{30}$ homolog linked to an in vivo indicating means is parenterally administered to a human subject. Parenteral administration includes intramuscular administration, intravenous administration, and administration into other body sites, such as synovial fluid. The amount of composition administered is sufficient to bind a detectable quantity of Mac-1 receptors. In preferred embodiments the $D_{30}$ homolog is $D_{30}$ fragment.

As used herein, the terms "label" and "indicating means" in their various grammatical forms refer to single atoms and molecules that are either directly or indirectly involved in the production of a detectable signal to indicate the presence of a complex. "In vivo" labels or indicating means are those useful within the body of a human subject. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents. Such labels are themselves well known in clinical diagnostic chemistry and constitute a part of this invention only insofar as they are utilized with otherwise novel proteins methods and/or systems.

The linking labels, i.e., labelling of, polypeptides and proteins is well known in the art. For instance, antibody molecules produced by a hybridoma can be labelled by metabolic incorporation of radioisotope-containing amino acids provided as a component in the culture medium. See, for example, Galfre et al., *Meth. Enzymol.*, 73:3–46 (1981). The techniques of protein conjugation or coupling through activated functional groups are particularly applicable. See, for example, Aurameas et al., *Scand. J. Immunol.*, Vol. 8, 7:7–23 (1978), Rodwell et al., Biotech., 3:889-894 (1984) and U.S. Pat. No. 4,493,795.

The subject is then maintained for a predetermined time period sufficient for the $D_{30}$ homolog to bind to the Mac-1 receptors present on the cells of the human subject and form a Mac-1 receptor:$D_{30}$ homolog complex. Preferably, this time period has been predetermined to optimize the formation of Mac-1 receptor:$D_{30}$ homolog complexes.

The subject is then assayed for the presence of and preferably the location of any Mac-1 receptor:$D_{30}$ homolog complexes formed.

EXAMPLES

The following examples are intended to illustrate, but not limit, the present invention.

1. Preparation of $D_{30}$ Fragment from Plasma Fibrinogen

A. Purification of Plasma Fibrinogen

Fibrinogen was isolated from fresh plasma by cold ethanol fractionation procedures. To one volume of plasma, 0.22 volumes of cold 50% ethanol, pH 7.0 was admixed which lowered the temperature to −3 degrees Celsius (−3° C.). The admixture was centrifuged and the resultant precipitate was washed with 0.5 original volumes (OV) of 7% ethanol, pH 6.5 at −3° C. The precipitate was re-collected and dissolved in 0.25 OV 0.55M trisodium citrate buffer, pH 6.5 at 30° C. The resultant solution was cooled to 0° C. and the fibrinogen was precipitated by the addition of cold 20% ethanol to a final concentration of 8% to form purified fibrinogen.

B. Proteolytic Digestion of Purified Fibrinogen

Fifty milligrams (mg) of purified fibrinogen was dissolved in 1 milliliter (ml) of a TBS buffer solution containing 0.01M Tris-HCl 0.14M NaCl pH 7.4, and was proteolytically digested by Streptokinase-activated plasminogen (plasmin) according to the following procedure.

Streptokinase-activated plasminogen was prepared by admixing plasminogen (KABI, 20 units (U)) to 2 ml of 0.1M sodium phosphate buffer, pH 7.4 and premaintaining for 10 minutes at 37° C. with 500U of streptokinase (Streptase, Behring). This solution was then admixed at a final concentration of 18 micrograms per ml (µg/ml) to the solution of purified fibrinogen in 2M urea.

The admixture was maintained for 2 hours at 37° C. The proteolytic reaction in the admixture was terminated by the addition of 50,000 U/ml trasylol (Sigma, St. Louis, Mo.). The resulting solution of fibrinogen fragments was extensively dialyzed against a solution of TBS for 24 hours at 4° C. The dialysis buffer was changed every 8 hours. The dialyzed solution was then recovered and applied on a Sephadex G-100 column (Pharmacia LKB, Piscataway, N.J.). The column chromatography was performed to separate the fragments resulting from the proteolytic digestion of fibrinogen. The column was prewashed with a running buffer of TBS followed by application of the dialyzed fibrinogen fragments. Fractions of 3 ml were collected and the molecular weights of the separated fragments of fractions were determined by 10% sodium dodecyl sulfate-polyacrylamide gel electrophoresis (SDS-PAGE) with and without reduction by 3% mercaptoethanol.

Three fragments of different molecular weights were visualized by Coomassie Blue staining of the gel. Fragments X, D, and E had respective molecular weights of approximately 240,000, 85,000, and 50,000 under non-reducing conditions. The fractions corresponding to the three separate peaks were separately pooled, dialyzed against distilled water, and concentrated by lyophilization.

C. Proteolytic Digestion of Fragment D to Produce a $D_{30}$Homolog

Fibrinogen fragment D with a molecular weight of 80,000 (80 kDa), purified and concentrated, was proteolytically digested with plasmin in 2M urea for 24 hours at 37C as described in Example 1B. The digestion was terminated and the resultant solution dialyzed as described in Example 1B. The dialyzed solution was recovered and the products of the digestion were isolated by high performance liquid chromatography (HPLC) on a mono-Q-column (Pharmacia) equilibrated in 0.01 M sodium phosphate, pH 7.0. The fragments were eluted with a solution of 0.01M sodium phosphate and 1 M sodium chloride, pH 7.0. The purity of the eluted proteins in the collected fractions was assayed on 15% SDS-PAGE under non-reducing conditions. Coomassie Blue staining of the gel revealed a 30 kDa fragment of greater than 90% homogeneity. The purified proteolytic digestion product of fragment D having a kDa of 30 was designated $D_{30}$. The peak fractions containing $D_{30}$ were pooled and concentrated by lyophilization to produce a $D_{30}$ homolog.

2. Binding of $D_{30}$ to the Mac-1 Receptor $D_{30}$ Binding Site

A. Labelling a $D_{30}$ Homolog

Iodogen was dissolved in dichloromethane for a final concentration of 1 µg/ml and 170 µl of dissolved iodogen was dried in the bottom of a glass tube. A $D_{30}$ homolog in this instance, purified as described in the Example 1C, was resuspended in 0.055M sodium citrate buffer, pH 7.4, for a final concentration of 5 µg/ml. Two hundred of dissolved $D_{30}$ solution was placed into the iodogen-coated tube with 700 µCi of carrier-free sodium iodide. The admixture was maintained on ice for 20 minutes with occasional agitation. To stop the iodination reaction, the admixture was removed from the tube and gel filtered on a Sepharose G-25 coarse column (100×2.5). Fractions of iodinated homolog were determined by trichloroacetic acid precipitable counts. The labelled $D_{30}$ homolog produced was radiolabelled to a specific activity of $4.5\times10^5$ counts per minute per µg of $D_{30}$ homolog.

B. Preparation of Cells

Blood was collected after informed consent from medication-free normal volunteers and anticoagulated with a mixture of 0.14M citric acid, 0.2M trisodium citrate, and 0.22M dextrose. The anticoagulated blood was centrifuged at 800×g for 15 minutes at room temperature and the platelet-rich plasma supernatant was discarded. The pelleted erythrocytes, mononuclear and polynuclear cells were resuspended and diluted with a volume equal to the starting blood volume with chilled 0.14M PBS, pH 7.4. The peripheral blood mononuclear cells (PBMC) were depleted from the diluted cell suspension by centrifugation on low endotoxin Ficoll-Hypaque (Sigma, St. Louis, Mo.) at 400×g for 10 minutes at 18C.

The polynuclear cells (neutrophils) in the PBMC -depleted cell suspension were then recovered by dextran sedimentation. The resulting cell pellet containing neutrophils was resuspended at a concentration of $1.5 \times 10^7$ cells/ml in serum-free RPMI 1640 (Irvine Scientific, Irvine, Calif.) supplemented with 20 mM Hepes [4-(2-hydroxyethyl)-1-piperidineethanesulfonic acid](Calbiochem Boehring, La Jolla, Calif.) in the presence of 2.5 mM calcium chloride and 100 mM D-phenyl-1-prolyl-1 arginine chloramethyl (PPack; Calbiochem Boehring). The resuspended cell suspension was maintained on ice and used within two hours of isolation.

C. Binding Assay with Iodinated $D_{30}$ Homolog and Stimulated Cells

Separate aliquots of the resuspended Mac-1 receptor-bearing neutrophils were stimulated with 10 μM of the chemotactic peptide formylmethionyl-leucyl-phenylalanine (fMLP, Sigma) immediately before admixing with increasing concentrations of $D_{30}$ homolog labelled with $^{125}I$ as described herein above. The concentration of $D_{30}$ in the admixture ranged from 1 μg/ml up to 20 μg/ml. The admixture was maintained for 20 minutes at room temperature after which time equilibrium was reached. Aliquots of the admixtures were then centrifuged through a mixture of silicon oils at 12,000×g for 5 minutes at room temperature to separate the free $D_{30}$ from the neutrophil-bound $D_{30}$. The total cell-associated radioactivity was determined by gamma counter detection.

Specific cell-associated binding of $D_{30}$ was calculated by subtracting the cell-associated radioactivity that resulted in admixtures maintained in the presence of 100-fold molar excess of unlabelled $D_{30}$ or fibrinogen from the total radioactivity. The net or specific results of the binding reaction of iodinated $D_{30}$ to neutrophils is shown in FIG. 2 where each point represents the mean ± the standard error of the mean (SEM) of three independent experiments. The results show that suspensions of stimulated Mac-1 receptor-bearing neutrophils bound iodinated $D_{30}$ in a specific and saturable reaction approaching steady state at 15–20 μg/ml of added iodinated $D_{30}$ with the association of approximately 136, 200±15 molecules of $D_{30}$ bound to each cell. Similar analyses were performed with aliquots of a monocytic-cultured cell line, THP-1, with ATCC accession number TIB 202, (ATCC, Bethesda, Md. ) with quantitatively identical results to those obtained with lymphocytes.

The binding of iodinated $D_{30}$ to Mac-1 on fMLP-stimulated suspensions of neutrophils was confirmed by performing inhibition assays with monoclonal antibodies described herein. A suspension of neutrophils at $1.5 \times 10^7$ cells/ml, which was prepared as described in Example 1B, was incubated with saturating concentrations of a monoclonal antibody directed against epitopes on either the α or β subunits of the Mac-1 receptor for 30 minutes at room temperature. The monoclonal antibody-incubated cell suspension was then treated with 10 μM fMLP as described in Example 1B. The stimulated cell suspension was then equilibrated with 5 μg/ml $^{125}I$-$D_{30}$ in the presence of 2.5 mM $CaCl_2$ and 100 μM PPACK for an additional 20 minutes at room temperature. The binding reaction was terminated as described above.

Monoclonal antibodies tested for their ability to inhibit the binding of $D_{30}$ to Mac-1 included the following: OKM1, M1/70 and 60.1, which are directed against different epitopes of the α subunit of the Mac-1 receptor; 60.3 and IB4, which are directed against the β subunit of the Mac-1 receptor. The anti-class I MHC W6/32 was used as the control antibody. Descriptions of the OKM1, M1/70, and 60.1 antibodies are respectively found in Wright et al., *Proc. Natl. Acad. Sci., USA*, 80:5699–5703 (1983), Ho et al., *J. Biol. Chem.*, 258:2766–2769 (1983), and Wallis et al., *Blood*, 67:1007–1013 (1986). The antibodies against the beta subunit are described in Price et al., *J. Immunol.*, 139:4174–4177 (1987) and Wright et al., supra.

Specific binding of $D_{30}$ to stimulated Mac-1 receptor-bearing neutrophils and inhibition of binding by treatment with Fab fragments of the monoclonal antibodies was calculated as described above. OKM1 and M1/70, both directed against the α subunit of Mac1, completely abolished the binding to $^{125}I$-$D_{30}$ to fMLP-stimulated suspensions of neutrophils. In contrast, monoclonal antibodies reacting with a different epitope on the α subunit, 60.1, or against the β subunit, 60.3 and IB4, did not interfere with $^{125}I$-$D_{30}$ binding to Mac-1.

3. Preparation of Anti-$D_{30}$ Monoclonal Antibodies.

$D_{30}$ is obtained and resuspended as described in Example 1C and 2A, respectively. Balb/c ByJ mice (Scripps Clinic and Research Foundation Vivarium, La Jolla, Calif.) are immunized intraperitoneally (i.p.) with 50 μg of prepared $D_{30}$ immunogens in complete Freund's adjuvant (CFA) followed by a second and third immunization using the same $D_{30}$ immunogen, each about three weeks apart, in incomplete Freund's adjuvant (IFA). The mice receive a boost of 50 μg of prepared $D_{30}$ immunogen intravenously (i.v.) in normal saline four days prior to fusion and a second similar perfusion boost one day later.

The animals so treated are sacrificed and the spleen of each mouse was harvested. A spleen cell suspension is then prepared. Spleen cells are then extracted from the spleen cell suspension by centrifugation for about 10 minutes at 1000 r.p.m., at 23° C. Following removal of supernatant, the cell pellet is resuspended in five ml cold $NH_4Cl$ lysing buffer, and is maintained for about 10 minutes.

To the lysed cell suspension are admixed 10 ml Dulbecco's Modified Eagle Medium (DMEM) (GIBCO) and Hepes buffer, and that admixture is centrifuged for about 10 minutes at 1000 r.p.m. at 23° C.

The supernatant is decanted, the pellet is resuspended in 15 ml of DMEM and Hepes and then centrifuged for about 10 minutes at 1000 r.p.m. at 23° C. The above procedure is repeated.

The pellet is then resuspended in 5 ml DMEM and Hepes. An aliquot of the spleen cell suspension is then removed for counting. Fusions are accomplished in the following manner using the non-secreting mouse myeloma cell line P3X63Ag8.653.1, a subclone of line P3X63Ag 8.653 (ATCC 1580). Using a myeloma to spleen cell ratio of about 1 to 10 or about 1 to 5, a sufficient quantity of myeloma cells are centrifuged into a pellet, washed twice in 15 ml DMEM and Hepes, and centrifuged for 10 minutes at 1000 r.p.m. at 23° C.

Spleen cells and myeloma cells are combined in round bottom 15 ml tubes. The cell mixture is centrifuged for 10 minutes at 1000 r.p.m. at 23° C., and the supernatant is removed by aspiration. Thereafter, 200 µl of 50 percent (weight per volume) aqueous polyethylene glycol 4000 molecular weight (PEG; ATCC Baltimore, Md.) at about 37° C. are admixed using a one ml pipette with vigorous stirring to disrupt the pellet, and the cells are gently mixed for between 15 and 30 seconds. The cell mixture is centrifuged four minutes at 700 r.p.m.

At about eight minutes for the time of admixing the PEG, five ml of DMEM plus Hepes buffer are admixed slowly to the pellet, without disturbing the cells. After one minute, the resulting admixture is broken up with a one ml pipette, and is incubated for an additional four minutes. This mixture is centrifuged for seven minutes at 1000 r.p.m. The supernatant is decanted, five ml of HT (hypoxanthine/thymidine) medium are slowly admixed to the pellet, and the admixture is maintained undisturbed for five minutes. The pellet is then broken into large chunks, and the final cell suspension is placed into T75 flasks (2.5 ml per flask) into which 7.5 ml HT medium have been placed previously. The resulting cell suspension is maintained at 37° C. to grow the fused cells. After 245 hours 10 ml of HT medium are admixed to the flasks, followed six hours later by admixture of 0.3 ml of 0.04 mM aminopterin. Forty-eight hours after fusion, 10 ml of HAT (hypoxanthine/aminopterin/thymidine) medium are admixed to the flasks.

Three days after fusion, viable cells are plated out in 96-well tissue culture plates at about $2 \times 10^4$ viable cells per well (768 total wells) in HAT buffer medium as described in Kennett et al., *Curr. Top. Microbiol. Immunol.*, 81:77 (1978). The cells are fed seven days after fusion with HAT medium and at approximately 4–5 day intervals thereafter as needed with HT medium. Growth is followed microscopically, and culture supernatants are collected about two weeks later and assayed for the presence of $D_{30}$-specific antibody by solid phase radioimmunoassay (RIA).

Briefly, 50 µl of PBS containing 5 µg/ml of the prepared $D_{30}$ immunogen is admixed into the wells of microtiter plates. The plates are maintained overnight (about 16 hours) at 4° C. to permit the $D_{30}$ immunogen to adhere to well walls. After washing the wells four times with SPRIA buffer (2.68 mM KCl, 1.47 mM $KH_2PO_4$ 137 mM NaCl, 8.03 mM $Na_2HPO_4$, 0.05% Tween-20, 0.1 KIU/ml Traysol, 0.1% BSA, of SPRIA buffer containing 3% normal goat serum (NGS) and 3% bovine serum albumin (BSA) are admixed to each well to block excess protein binding sites. The plates are maintained for 30 minutes at 20° C., the wells emptied by shaking, and blotted dry to form a solid-support, i.e., a solid matrix to which immunogen is operatively affixed.

To each well is then admixed 50 µl of hybridoma tissue culture supernatant to form a solid-liquid phase immunoreaction admixture. The admixture is maintained for 2 hours at 37° C. to permit formation of solid-phase immunoreaction products. After washing the wells as described above, 50 µl of $^{125}$I-labelled goat anti-mouse IgG at 0.25 µg protein/ml are admixed to each well to form a labelling reaction admixture. Radioiodination of immunochemically purified goat anti-mouse IgG is performed enzymatically utilizing the Iodogen iodination procedure as described in Example 2A. The resultant admixture is maintained for one hour at 37° C. to permit formation of $^{125}$I-labelled solid-phase immunoreaction products. After washing the wells as described above, the amount of $^{125}$I-labelled product bound to each well is determined by gamma detection.

Hybridomas are selected from hybridoma cultures that secrete anti-$D_{30}$ antibodies into their culture media, and further characterized as described herein.

4. $D_{30}$ Antibody Molecule Production and Purification.

Hybridoma anti-$D_{30}$ is cultured in a 5% $CO_2$ humidified atmosphere at 37° C. in DMEM containing 2 mM L-glutamine, 50 µg/ml gentamycin, 10% fetal bovine serum, 10% horse serum, all from Grand Island Biological Co., Lawrence, Mass., 10% NCTC medium from Microbiological Associates, Rockville, Md., 1 mM hypoxanthine and 0.3 mM thymidine, both from Sigma Chemical Corp., St. Louis, Mo. Cell concentration is kept in the range of about $1-2 \times 10^5$ cells per ml of medium to about $1-2 \times 10^6$ cells per ml of medium for cell growth, division, and production of antibody.

To produce ascites tumor fluid containing anti-$D_{30}$ antibody molecules, 10-week old Balb/c mice are immunologically primed by intraperitoneal injection with 0.3 ml of mineral oil and subsequently intraperitoneally injected with $3-5 \times 10^5$ anti-$D_{30}$ hybridoma cells. The inoculated mice are then maintained for a time period sufficient for anti-$D_{30}$ antibody-containing ascites tumor fluids to accumulate, e.g., for about 10 to about 21 days. The ascites fluid is collected and clarified by centrifugation at 15,000×g for one hour at 4° C. and stored frozen at −20° C.

Anti-$D_{30}$ antibody molecules are isolated from the ascites fluid by subjecting the fluid to fast protein liquid chromatography (FPLC) on a Pharmacia Mono QHR 5/5 anion exchange column in a Pharmacia FPLC System (both from Pharmacia) using a 0–0.5M NaCl gradient in 10 mM Tris-HCl pH 8.0, and following the directions supplied with the column. The anti-$D_{30}$ antibody molecules so isolated can then be transferred to any physiologically tolerable diluent desired by dialysis.

Alternatively, anti-$D_{30}$ antibody molecules can be isolated from the ascites tumor fluid by precipitation with ammonium sulfate according to the method described by Goding, *Monoclonal Antibodies: Principles and Practice*, Academic Press, p100–101 (1983). Briefly, that method entails slowly admixing saturated ammonium sulfate to the ascites fluid until about a 45% to about a 50% ammonium sulfate concentration is achieved. The precipitated immunoglobulins are then collected by centrifugation at 2000×g, preferably 10,000×g. The precipitate is washed 2 or 3 times in 40% saturated ammonium sulfate. The precipitated anti-$D_{30}$ antibody molecules are then dialyzed against 500–1000 volumes of phosphate buffered saline (PBS) or any other physiologically tolerable diluent desired to remove ammonium sulfate. The dialysis fluid is changed several times at intervals of a few hours. The protein concentration of the recovered dialyzed anti-$D_{30}$ antibody solution is determined by the Lowry method [Lowry et al., *J. Biol. Chem.*, 193, 265–275 (1951)] using a bovine serum albumin standard.

5. Preparation of an Anti-($D_{30}$ Idiotype) Antibody.

Three hundred µg of the recovered dialyzed solution containing anti-$D_{30}$ monoclonal antibodies as obtained in Example 4 are emulsified in CFA and injected subcutaneously in multiple sites along the mammary chain of a female New Zealand white rabbit which was prebled to obtain pre-immune serum. Purification of pre-immune serum is performed as described below. Two intramuscular boosters of 100 µg of antibody in PBS are given on days 7 and 30, and sera are collected 10 days later. The sera obtained are extensively absorbed on pooled mouse Ig (Cappel Laboratories, Cochranville, Pa.), followed by mouse IgG2a and IgG2b coupled to Sepharose 4B (Pharmacia Chemicals). When no further protein can be eluted from these immunoadsorbents with 0.5N acetic acid, the flow-through is adsorbed to and eluted from 5 mg of purified anti-$D_{30}$ monoclonal antibodies, prepared as described in Example 4, coupled to Sepharose 4B. The eluate is concentrated by sodium sulfate at a final concentration of 18% (wt/vol), dialyzed against PBS, and stored at 4° C. until used. Immunoglobulin eluted from the column is detected by a radioimmunoassay (RIA).

A solid-phase RIA is used to measure the binding of purified anti-($D_{30}$ idiotype) antibody to fixed anti-$D_{30}$ monoclonal antibodies. Anti-$D_{30}$ monoclonal antibodies are diluted (1:1,000 to 1:16,000, depending on the ascites fluid concentration) in carbonate-bicarbonate buffer (pH 8.9), and 25 µl aliquots are added to wells of polyvinyl microtiter plates (Dynatech Laboratories). These antibodies are allowed to dry in the wells by overnight incubation at 37C. The free binding sites on the wells are blocked for at least 1 hour with 10% agamma horse serum (GIBCO Laboratories, Grand Island, N.Y.) dissolved in PBS containing 0.08% sodium azide. Dilutions (25 µl) of anti-($D_{30}$ idiotype) antibodies are added, and after one hour at room temperature the plates are washed extensively.

Bound anti-($D_{30}$ idiotype) antibodies are detected by adding 25 µl (30,000 cpm) of $^{125}$I-labelled goat anti-rabbit IgG (Cappel Laboratories) labelled by the Iodogen method as described in Example 2A. The admixture is maintained for an additional one hour at room temperature. All dilutions of anti-($D_{30}$ idiotype) antibodies or radiolabelled probe are made in 10% agamma horse serum dissolved in PBS containing 0.08% sodium azide. The plates are washed free of unbound probe, and the radioactivity bound to individual wells is measured with a gamma counter and compared to the radioactivity bound to wells in which control preimmune serum is used in place of anti-$D_{30}$ monoclonal antibodies.

Monoclonal anti-($D_{30}$ idiotype) antibody compositions are also generated by immunizing Balb/c mice, as described in Example 3, with anti-$D_{30}$ monoclonal antibodies prepared as described above. Subsequent injections and fusions are performed as described in Example 3. Detection of anti-($D_{30}$ idiotype) antibodies secreted by hybridomas is performed as described hereinbefore. Production and purification of anti-($D_{30}$ idiotype) antibodies is performed as described in Example 4.

Confirmation of functional anti-($D_{30}$ idiotype) antibody specificity in either a serum sample or hybridoma culture supernatant is determined in binding assays to Mac-1 receptor-expressing lymphocytes as described in Example 2 or in competition assays as described in Example 6.

6. Competition of Binding of $D_{30}$ Fragments to Mac-1 $D_{30}$ Binding Site on Neutrophils Fibrinogen was purified as described in Example 1 and radiolabelled as described for $D_{30}$ in Example 2A. Mac-1 receptor-bearing neutrophils were prepared as described in 2B. Separate aliquots of stimulated neutrophils at a concentration of 1.5×10$^7$ cells/ml were simultaneously incubated with a predetermined subsaturating dose of $^{125}$I-labelled fibrinogen (50 µg/ml) and increasing concentrations of various competing proteins for 20 minutes at room temperature. The reaction in the admixture was terminated by centrifugation through silicon oils as described in Example 2. The amount of labelled Mac-1 receptor:fibrinogen complex was determined by gamma detection. Non-specific binding was calculated as described in Example 2 and subtracted from the total to calculate specific binding.

Figure 3:
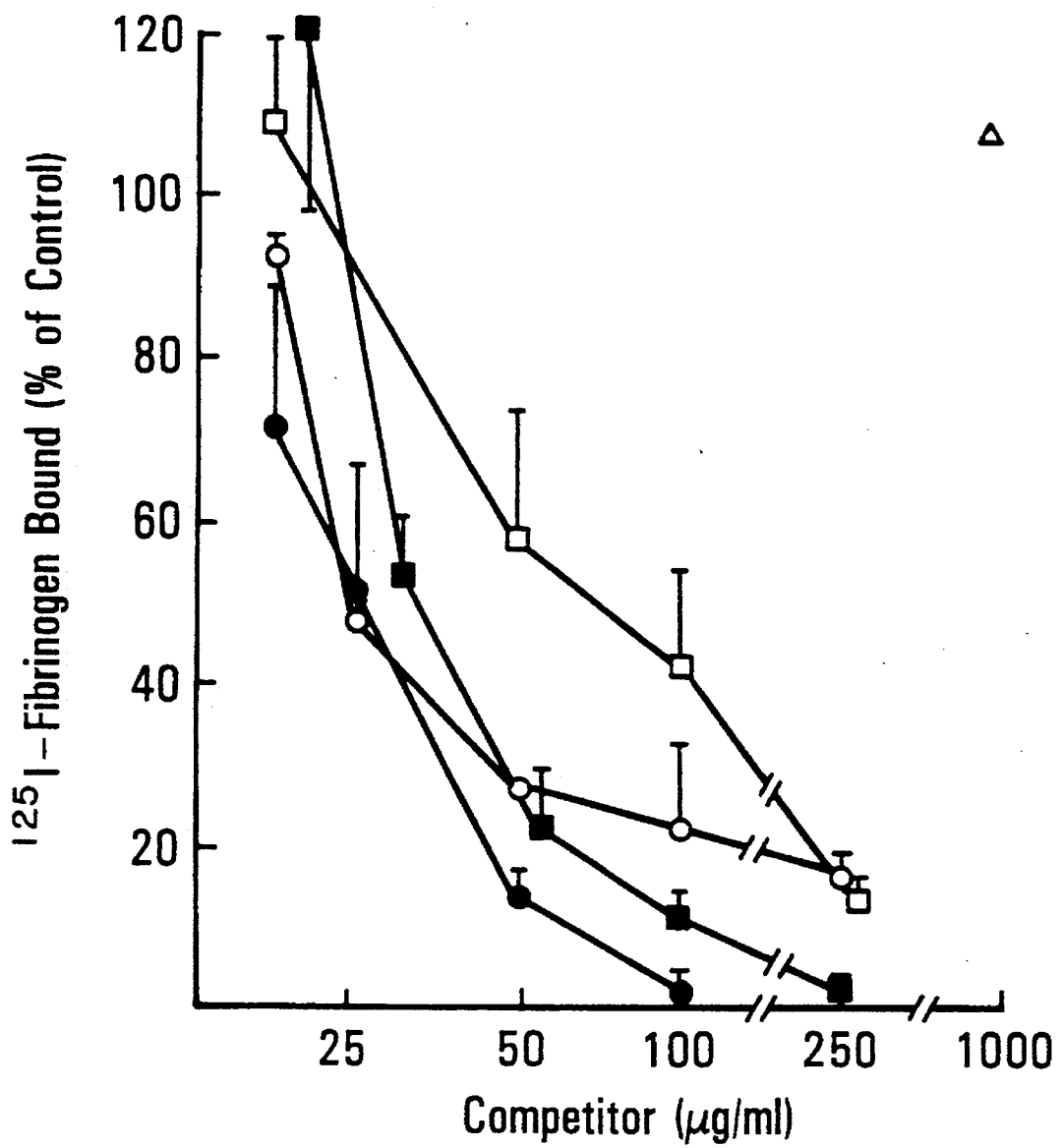

Unlabelled fibrinogen and fibrinogen fragments X, D:E and D obtained as described in Example 1A and B were evaluated for their ability to compete for labelled fibrinogen binding to stimulated neutrophils. All four protein compositions inhibited the binding of $^{125}$I-fibrinogen to stimulated neutrophils in a concentration-dependent fashion with a IC$_{50}$ ranging between 25–50 µg/ml of added competitor as shown in FIG. 3. $^{125}$I-fibrinogen specifically bound to cells in the absence of competitors at a concentration of 80,200±8,000 molecules/cell. A one mM solution of RGD, under the same experimental conditions, did not inhibit $^{125}$I-fibrinogen binding to neutrophils.

Figure 4:
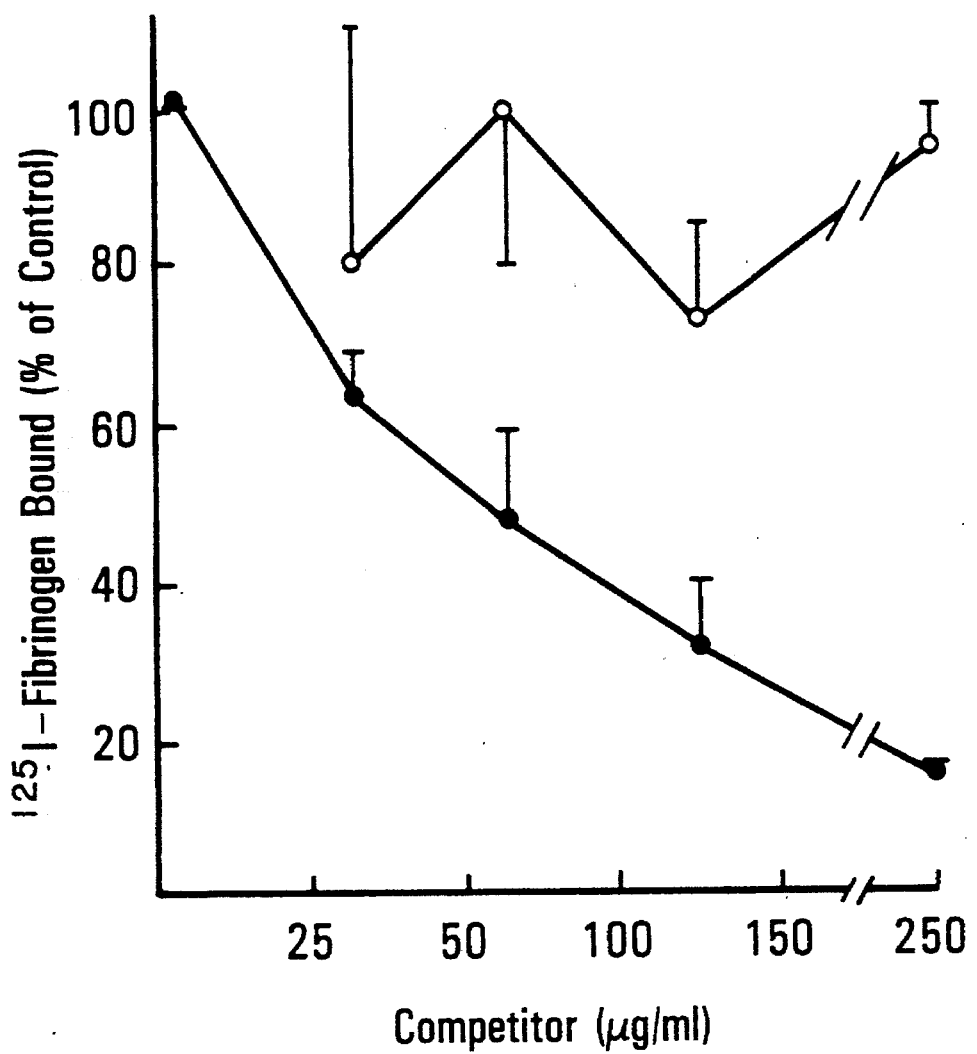

Fibrinogen fragments E and $D_{30}$ obtained as described in Example 1B were evaluated for their ability to compete for labelled fibrinogen binding to stimulated neutrophils. The results of three independent experiments, shown in FIG. 4, reveal that increasing concentrations of $D_{30}$ produce dose-dependent inhibition of $^{125}$I-fibrinogen binding to stimulated cells with an IC$_{50 = 50}$ µg/ml, while under the same experimental conditions, fragment E was ineffective. $^{125}$I-fibrinogen bound in the absence of competitors was 99,600±4,500 molecules/cell.

Purified anti-($D_{30}$ idiotype) antibodies are also evaluated as competitive inhibitors of $^{125}$I-fibrinogen binding to Mac-1 receptor-bearing stimulated neutrophils as described herein before. The anti-($D_{30}$ idiotype) antibodies are evaluated over a subsaturating to saturating concentration range. The amount of labelled $^{125}$I-fibrinogen:Mac-1 complex is determined as described above.

7. Preparation of an Anti-(Mac-1:$D_{30}$ Homolog Complex)

A $D_{30}$ homolog is purified and labelled as described in Example 1 and 2A, respectively. Neutrophils bearing Mac-1 receptors are obtained and stimulated as described in Example 2B. Binding assays of labelled $D_{30}$ to stimulated neutrophils are performed as described in Example 2C with the exception that the predetermined optimal concentration of labelled $D_{30}$, 20 mg/ml, is admixed with 10×10$^6$ stimulated neutrophils. Assays to verify binding are performed as described in Example 2C. Separate aliquots of unlabelled $D_{30}$ homolog:Mac-1 receptor-bearing neutrophils are diluted in PBS, then injected into the peritoneal cavity of Balb/c mice. The injection protocol for generating an immune response is described in Example 3. Antibody titers in serum samples at one week periods post-boost are determined in the assay as described below. Mice which exhibit high anti-(Mac-1:$D_{30}$ homolog) titers are then sacrificed and the spleens of each are harvested and fused as described in Example 3 to generate monoclonal antibodies against Mac-1:$D_{30}$ homolog complex.

Growing hybridoma clones are screened for the production of antibodies to only Mac-1:$D_{30}$ complex in two assays. Separate aliquots of hybridoma culture supernatants are admixed with either unoccupied Mac-1 receptor-bearing neutrophils or $D_{30}$ homolog:Mac-1 receptor-bearing neutrophils. Reaction of the monoclonal antibodies with the neutrophil surface is analyzed by indirect staining of the cell suspension. Briefly, 1×106 neutrophils are incubated in V-bottomed microtiter plates (Costar Corp., Cambridge, Mass.) with predetermined saturating concentrations of each antibody tested for 30 minutes at 4° C. After washes with RPMI 1640 containing 10% FCS, cells are maintained with fluorescein-conjugated goat F(ab)$_2$ anti-mouse IgG for an additional 30 minutes at 4° C. After washes in RPMI 1640, specific binding of monoclonal antibodies to the cell surface is analyzed by flow cytometry on a Becton Dickinson IV/40 fluorescence activated cell sorter.

Only supernatants from hybridomas which react with neutrophils bearing Mac-1:D$_{30}$ homolog complex are screened in solid phase RIAs as described in Example 3 where 5 μg/ml of D$_{30}$ is affixed to wells in microtiter plates.

Hybridomas secreting antibodies which only react with D$_{30}$ homolog:Mac-1 receptor-bearing neutrophils and not unoccupied Mac-1 receptor-bearing neutrophils or isolated D$_{30}$ are expanded. Antibodies secreted therefrom are purified as described in Example 4. Only these purified antibodies against Mac-1:D$_{30}$ homolog complex are used in diagnostic assays to detect such complexes as on cell surfaces in question. The diagnostic assays are performed as described hereinabove.

Anti-(Mac-1:D$_{30}$ homolog complex) antibodies selected for use bind the Mac-1:D$_{30}$ homolog complex as determined by diagnostic assays and these antibodies do not bind a D$_{30}$ homolog or the Mac-1 receptor alone.

8. Characterization of the Mac-1 Receptor Binding Site on the Gamma Chain of D$_{30}$ Fragment of Fibrinogen A. Inhibition of D$_{30}$ Binding to Mac-1 with a Gamma Chain Specific Polyclonal Antibody A polyclonal antibody directed against the gamma chain of fibrinogen was made by injecting the immunogen, purified gamma chain cyanogen bromide produced fragment consisting of amino acid residue sequence from residue 95 to residue 264 as shown in FIGS. 1B–1 through 1B–3) into mice as described by Fair et al., *J. Biol. Chem.*, 256:8018–8023 (1981). The polyclonal antibody was shown to recognize the epitope defined by the amino acid residue sequence of the gamma chain beginning with amino acid residue 95 and ending with 264 as shown in FIGS. 1B–1 through 1B–3) The binding of $^{125}$I-D$_{30}$ fragment to Mac-1 receptor-bearing monocytes as prepared in Example 8D was inhibited by the polyclonal antibody in experiments performed as described in Example 6.

The Mac-1 receptor binding site on D$_{30}$ was further defined by digesting D$_{30}$ with chymotrypsin for 30 minutes. The resultant digested D$_{30}$ fragment was shown to not inhibit the binding of fibrinogen to Mac-1-receptor-bearing monocytes. In addition, the digested D$_{30}$ fragment was not recognized by polyclonal antibody which recognizes the 94–264 amino acid residue sequence of the gamma chain. Microsequencing of the fragment showed that the amino acid residue Arginine at residue position 247 comprised the amino terminus. Thus, the epitope defined by the polyclonal antibody was narrowed to the amino acid residue sequence beginning at 94 and ending at 247 excluding the amino acid residue sequence between residue 247 and 264.

B. Polypeptide Synthesis

Polypeptides derived from the gamma chain of the D$_{30}$ fragment of fibrinogen and restricted to the epitope mapped by the polyclonal antibody were synthesized using the classical solid-phase technique described by Merrifield, *Adv. Enzymol.*, 32:221–296 (1969) as adapted for use with a model 430 automated peptide synthesizer (Applied Biosystems, Foster City, Calif.). The amino acid residue sequences of the synthesized polypeptides are listed in Table 1 with their designated SEQ ID NO. The residue numbers corresponding to specific regions in the native gamma chain of D$_{30}$ are also shown for each polypeptide. The polypeptides with SEQ ID NO 12 and 13 were synthesized with an additional N-terminal tripeptide, lysine-tyrosine-glycine. The polypeptide with SEQ ID NO 11 was synthesized with a single glycine. The lysine, tyrosine and glycine residues were added to allow for coupling reactions, for labelling of the synthetic polypeptide with $^{125}$I and for adding a spacer, respectively. The polypeptides with SEQ ID NO 4 through 9 were synthesized with a C-terminal cysteine residue to add stability to the polypeptide. Prepared polypeptide resins were cleaved by hydrogen fluoride, extracted and analyzed for purity by high-performance liquid chromatography (HPLC) using a reverse-phase C18 column manufactured by Waters Associates, Milford, Mass.

TABLE 1

| Name[1] | SEQ ID NO | AMINO ACID RESIDUE SEQUENCE[2] | ACTIVITY[3] |
|---|---|---|---|
| DI | 3 | $^{169}$IKPLKANQQFLVYCEIDGSGNG$^{190}$ | 0 |
| DII | 3 | $^{195}$QKRLDGSVDFKK$^{206}$ | 3+ |
| DII | 3 | $^{161}$KQSGLYFIYPLKAN$^{174}$ | 0 |
| DIV | 4 | $^{185}$DGSGNGWTVFQKR$^{197}$ | 0 · |
| G1 | 5 | $^{89}$MLEEIMKYEASILTHDSC$^{185}$* | 0 |
| G2 | 6 | $^{103}$HDSSIRYLQEIYNSNNQC$^{119}$* | 0 |
| G3 | 7 | $^{117}$NNQKIVNLKEKVAQLEAC$^{133}$* | 0 |
| G4 | 8 | $^{131}$LEAQCQEPCKDTVQIHDC$^{147}$* | 0 |
| G5 | 9 | $^{145}$IHDITGKDCQDIANKGAC$^{61}$* | 0 |
| G6 | 10 | $^{169}$GLYFIKPLKANQQFLVYCEIDGSGC$^{188}$* | 0 |
| G7 | 11 | $^{195}$GQKRLDGSVDFKK$^{206}$** | 3+ |
| G8 | 3 | $^{191}$WTVFQKRLDGSV$^{202}$ | 3+ |
| G9 | 3 | $^{200}$GSVDFKKNWIQY$^{211}$ | 0 |
| G10 | 11 | $^{195}$GQKRLDGS$^{201}$** | 3+ |
| G11 | 3 | $^{202}$VDFKKN$^{207}$ | 0 |
| P1 | 12 | $^{191}$KYGWTVFQKRLDGSV$^{202}$*** | 3+ |
| P1b | 13 | $^{195}$KYGQKRLDGS$^{201}$*** | 3+ |

[1]Designation of polypeptides

TABLE 1-continued

| Name[1] | SEQ ID NO | AMINO ACID RESIDUE SEQUENCE[2] | ACTIVITY[3] |
| --- | --- | --- | --- |

[2]Numbers bordering the amino acid residue sequence indicate the corresponding region of the gamma chain of fibrinogen shown in (FIGS. 1B-1 through 1B-3) and listed as SEQ ID NO 3.
[3]Ability to promote cell attachment: Zero - no cell attachment; 3+ maximum cell attachment; See Example 8A for discussion
*A C-terminal cysteine residue was added to the polypeptide sequence.
**A N-terminal glycine residue was added to the polypeptide sequence.
***A tripeptide sequence of lysine-tyrosine-glycine was added to the N-terminus of the peptide.

C. Ability of Polypeptides to Promote Cell Attachment

To determine the Mac-1 receptor-binding site on the gamma chain of $D_{30}$, the synthetic polypeptides prepared above were separately evaluated in cell attachment assays. For these assays, wells of 96-well microtiter plates (Linbro/Titertek; Flow Laboratories, VA) were coated with 60 µl of a 1 mg/ml solution of individual synthetic polypeptides prepared above. The wells containing the dissolved polypeptides were maintained for 16 hours at 4° C. The wells were then washed twice with PBS and blocked for 30 minutes with 0.1% BSA in PBS. After a final wash, 100 µl of DMEM containing 1% fetal bovine serum and $2\times10^5$ cells/ml of either neutrophils or monocytes prepared respectively in Example 2B and Example 8D were admixed into each well. The cells were maintained for 30 minutes at room temperature to allow the cells to attach to the polypeptide-coated wells. Non-adherant cells were removed from the wells by washing twice with PBS. Adherent wells were fixed for 20 minutes with 3% paraformaldehyde at room temperature.

Adherent cells were quantitated by staining with 0.5% crystal violet. The plates were rinsed once to remove excess stain before drying. The stain remaining in the wells was then solubilized in 0.1M citric acid in 50% ethanol, pH 4.2. The optical density (O.D.) at 550 nm was determined with an ELISA reader (Biotek Instruments). Non-specific adherence was determined by plating cells on BSA-coated wells for the appropriate period of time. Specific adhesion to a given polypeptide substrate was calculated by subtracting the O.D. obtained with cells plated on BSA from that observed for cells plated on individual polypeptides.

Alternatively, the stained cells were examined visually under an inverted microscope with a 20×objective lens. The wells were scored as zero if no cells were attached and +if the well was covered with cells as listed in Table 1. Polypeptides promoting cells attachment included DII, G7, G8, G10, P1 and P1b as shown in Table 1. The specificity of the receptor-binding site defined by these cell-attachment promoting polypeptides was further characterized in the binding and inhibition of binding assays described below. The polypeptides used in the assays are subsequently referred to by the "Polypeptide Designation" as indicated in Table 1 and not by their SEQ ID NO.

D. Binding and Inhibition of Binding of P1 Polypeptide to Monocytes and THP-1 Cells

1) Monocytes

Anticoagulated blood was prepared as described in Example 2B. After resuspending the pelleted erythrocytes, mononuclear and polynuclear cells with a volume equal to the starting blood volume with chilled 0.14M PBS, 35 ml of the cell suspension were layered onto 15 ml of Ficoll-Hypaque (Pharmacia) in a 50 ml polypropylene tube and centrifuged at 400×g for 40 minutes at room temperature. The cells at the interface were carefully removed with sterile plastic pipettes and were then washed two times with excess 5 mM PBS-EDTA (ethylene diamine tetracetic acid). The washed cells were then centrifuged first at 400×g for 20 minutes at 4° C., the pellet was resuspended as above, then the suspension was centrifuged again at 120×g for 12 minutes at 4° C. The cell pellet was again resuspended to form a PMBC cell suspension.

To remove further platelet contaminants as described by Pawlowski et al., *J. Exp. Med.*, 158:393–412 (1983), the PMBC cell suspension was maintained twice at 37° C for 15 minutes in autologous serum supplemented with 5 mM EDTA. Cells were then recovered by centrifugation at 400×g for 15 minutes at room temperature and resuspended in RPMI1640 medium containing 50 U/ml penicillin, 0.125 ng/ml fungizone and 50 µg/ml streptomycin plus 10% autologous serum to give $8\times10^6$ cells/mi. Autologous serum was prepared by allowing the blood to clot in plastic tubes at 37° C for at least 120 minutes followed by centrifugation at 3200×g for 15 minutes at room temperature.

Human monocytes were purified from the platelet-free PMBC cell suspension as described by Fischer et al., Academic Press, Inc., New York, pp: 43–47 (1981). Briefly, 5 ml of the purified PMBC cell suspension at $8\times10^6$ cells/ml were layered on a plate precoated with autologous serum and maintained for 60 minutes at 37° C. At the end of the maintenance period, the medium, containing mostly lymphocytes, was removed. The plates were washed with four to five rapid changes of RPMI 1640 prewarmed to 37° C. Four ml of an EDTA solution was added and maintained for 15 minutes at room temperature. One ml of autologous serum was then admixed into the plates and the loosely adherent monocytes were scraped off the plate with a rubber policeman. Monocytes from several plates were pooled, centrifuged at 400×g for 10 minutes at 4° C and resuspended in RPMI 1640 containing 10% autologous serum to result in a final concentration of $1.5\times10^7$ purified monocytes/ml. The resuspended monocytes were maintained at 4° C until use. The purity of the monocyte preparation was greater than 90% as assessed by alpha-naphthyl acetate esterase staining and the viability was greater than 95% as judged by trypan blue exclusion.

For the binding assay, the synthetic radiolabelled polypeptide P1 (SEQ ID NO 12), that promoted cell attachment as described above, was tested for the ability to bind to monocytes in the presence of either cold P1 or an irrelevant polypeptide, L10 (LGGAKQAGDV, SEQ ID NO 14). P1 was radiolabelled with $^{125}$I as described in Example 2A with the exception that the labelled polypeptide was then purified from non-incorporated label by gel filtration over a Bio-Gel P2 column (Bio-Rad, Richmond, Calif.). The resultant radiolabelled P1 polypeptide was then used in the binding assay at a total of 20,000 counts per minute (cpm).

The binding assay was performed as described in Example 6 with the exception that 1 mg/ml of either cold P1 or L10 polypeptide was admixed simultaneously with 20,000 cpm of $^{125}$I-P1 to a one ml of a monocyte cell suspension containing $1.5 \times 10^7$ cells/ml.

Figure 5:
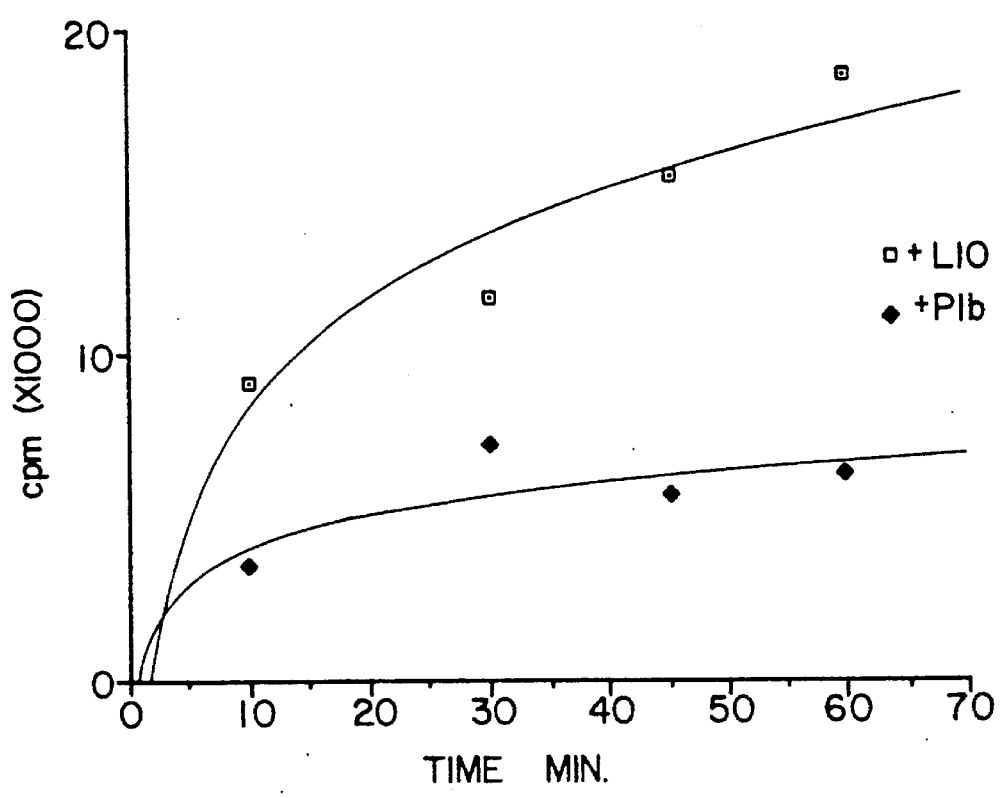

The specific cell-associated binding of radiolabelled P1 to monocytes was measured over 60 minutes at 10 minute intervals and was calculated as described in Example 6. The results of the binding assay are shown in FIG. 5. The amount of bound radiolabelled P1 is plotted on the ordinate in cpm X 000 against assay time plotted on the abscissa. Each point represents the mean ± the standard error of the mean (SEM) of three independent experiments. The results demonstrate that labelled P1 binds to monocytes in a non-saturable curve over the course of a one hour assay, the binding of which was competed by cold P1 but not by an irrelevant polypeptide, L10. Thus, the P1 polypeptide derived from the gamma chain of $D_{30}$ contains the binding site for the Mac-1 receptor on monocytes.

2) THP-1 Cells

Similar binding assays and inhibition thereof were performed using the monocytic cell line THP-1 (ATCC TIB 202, Bethesda, Md.). THP-1 cells were maintained in RPMI 1640 supplemented with 10% fetal bovine serum (HyClone, Logan, UT), 20 mM Hepes, 100 µg/ml gentamycin, 2 mM L-glutamine and 10 µM beta-mercaptoethanol. The competitive inhibitors evaluated in the assay to compete for the binding of the labeled P1 polypeptide to THP-1 cells included the following: $D_{30}$ prepared as described in Example 1; the irrelevant polypeptide L10 described above; the monoclonal antibody IB4 which recognizes the beta subunit of the Mac-1 receptor (Wright et al., *Proc. Natl. Acad. Sci., USA*, 80:5699–5703 (1983); the monoclonal antibody M1/70 which recognizes the alpha subunit of the Mac-1 receptor (Ho et al., *J. Biol. Chem.*, 258:2766–2769 (1983); and a monoclonal antibody against tissue factor as described by Morrisey et al., *Thromb. Res.*, 52:247–261 (1988).

The assays in which $D_{30}$ or polypeptides derived therefrom were performed as described above and in Example 6. The assays in which antibodies were used as competitive inhibitors were performed as described in Example 2C using 50 µg/ml of each antibody. Intact IgGs and not Fab fragments were used in these assays. The amount of binding of radiolabelled P1 polypeptide to THP-1 cells was measured after a one hour minute maintenance period in the absence or presence of unlabelled competitors.

Figure 6:
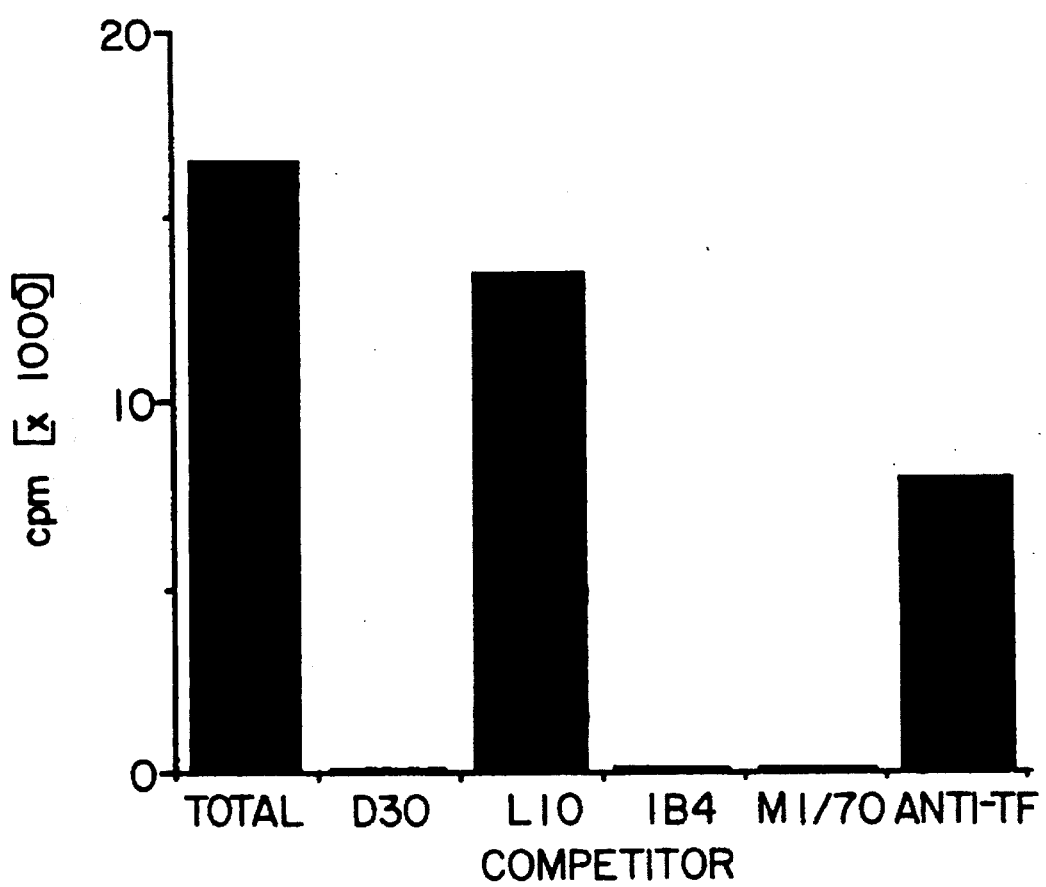

The results of these binding and inhibition of binding assays are shown in FIG. 6. The amount of inhibition by the individual competitors is compared to the total amount of specific binding of P1 in the absence of competitors which was approximately 16,000 cpm. $D_{30}$, IB4 and M1/70 completely inhibited the binding of P1 to THP-1 cells while anti-tissue factor antibody resulted in partial inhibition. The irrelevant polypeptide, L10, did not result in significant inhibition. Thus, the $D_{30}$ fragment containing portions of the alpha, beta and gamma chains of fibrinogen bound to the Mac-1 receptor on THP-1 cells and blocked the binding of labelled P1. Similarly, IB4 and M1/70 bound to the beta and alpha subunits of Mac-1 receptor, respectively, and blocked the binding of P1 to the receptor.

E. Inhibition of Fibrinogen Binding to THP-1 by P1 Polypeptide

The specificity of the P1 polypeptide for the Mac-1 receptor on THP-1 cells was confirmed in assays where the binding of purified intact fibrinogen to THP-1 cells was inhibited by P1 but not by the irrelevant polypeptide, L10. The assays were performed as described in Example 6 with the exception that THP-1 cells prepared as described in Example 8D were used instead of neutrophils. The amount of polypeptide used in the assay ranged in concentration from 7 µg/ml up to 60 µg/ml.

Figure 7:
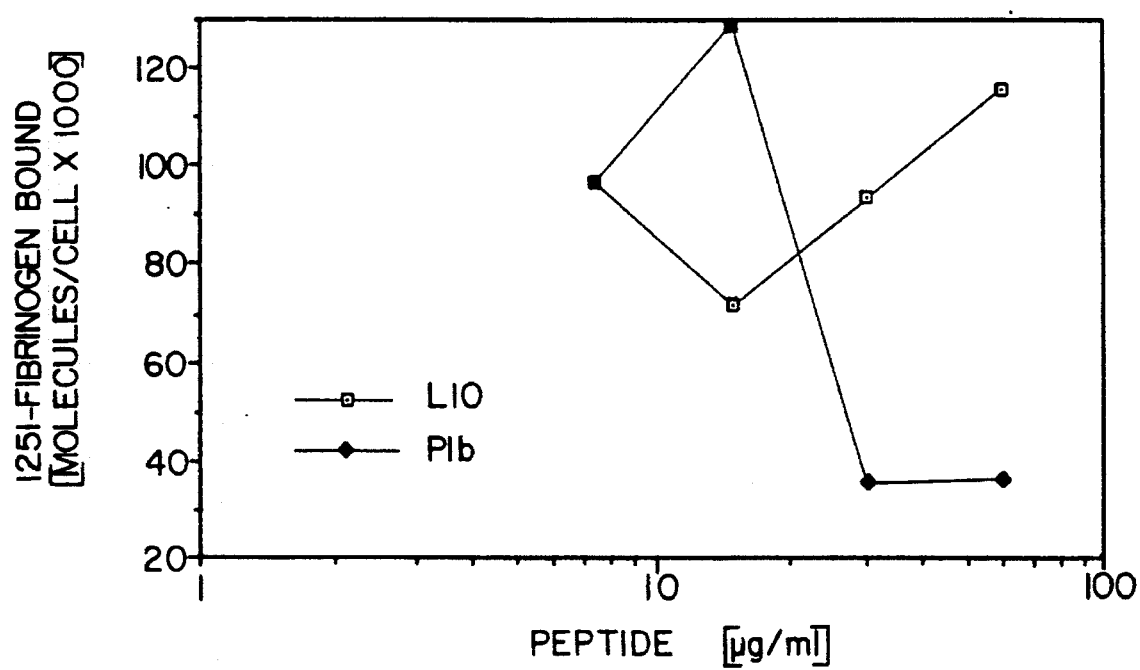

The amount of radiolabelled fibrinogen bound to THP-1 cells was expressed as molecules/cell $\times 1000$ and plotted on the ordinate against increasing polypeptide concentrations as shown in FIG. 7. P1 maximally inhibited the binding of fibrinogen to THP-1 cells at a concentration of 20 µg/ml as compared to the lack of inhibition by L10. These results confirm that the amino acid residue sequence required to allow binding of fibrinogen to its integrin receptor, Mac-1, is contained with the region from residue 191 to 202 of the gamma chain of the $D_{30}$ fragment of fibrinogen.

F. Inhibition of THP-1 Cell Attachment to Fibrinogen by P1 and P1 Polypeptides

Cell attachment assays were performed to determine if the P1b polypeptide (SEQ ID NO 13) which was derived from the gamma chain of $D_{30}$ from residue 195 to residue 201 would inhibit the binding of THP-1 cells to fibrinogen-coated plates as effectively as the larger polypeptide, P1 (SEQ ID NO 12). The assays were performed as described in Example 8C with the following modifications: the microtiter wells were coated with 10 µg/ml of fibrinogen overnight at room temperature to form fibrinogen-coated wells; the unoccupied sites on the wells were then blocked to prevent non-specific background with 3% gelatin for 30 minutes at room temperature; $2 \times 10^5$ THP-1 cells prepared as described in Example 8D2) were separately admixed with the polypeptides P1, P1 and L10, the latter of which served as a control, ranging in concentration from 0.03 mg/ml to 1 mg/ml to form THP-1 cell-polypeptide admixtures; the resultant admixtures were maintained for 30 minutes at room temperature after which time the cells were admixed to the fibrinogen-coated plates as described in Example 8C.

TABLE 2

Inhibition of THP-1 cell attachment to fibrinogen by
P1 and P1b gamma chain-derived polypeptides

| Concentration of polypeptide in mg/ml | Absorbance at 600 nm[1] | | |
|---|---|---|---|
| | P1 | P1b | L10 |
| 0.03 | 1.02 | 0.52 | 1.38 |
| 0.60 | 1.12 | 0.43 | 0.90 |
| 0.125 | 0.42 | 0.35 | 1.37 |
| 0.5 | 0.36 | 0.50 | 0.93 |
| 1.0 | 0.48 | 0.44 | 1.00 |

[1]Values in polypeptide columns indicate absorbance at an OD of 600 nm which is a measure of the amount of stain picked up by THP-1 cells attached to fibrinogen-coated wells; the greater the absorbance, the greater the number of attached cells, the less the inhibitory effect of the polypeptides.

The results of the inhibition of cell attachment assay are shown above in Table 2. The absorbance of crystal violet stain, indicating the relative number of cells that attached to the fibrinogen-coated wells, was measured at 600 nm. The absorbance values are tabulated in columns according to the concentration of each polypeptide separately tested in the assay. P1 at a concentration of 0,125 mg/ml maximally inhibited the binding of THP-1 cells to fibrinogen. In contrast, the smaller polypeptide, P1, was effective at inhibiting cell attachment at all concentrations of polypeptide tested.

L10, the irrelevant polypeptide, did not significantly inhibit cell attachment at any concentration of polypeptide. Thus, the minimal amino acid residue sequence required to promote the attachment of fibrinogen to the Mac-1 receptor on THP-1 monocytic cell line or on monocytes is from amino acid residue number 195 to amino acid residue number 201 as determined from the complete inhibition of THP-1 cells to fibrinogen by the P1b polypeptide. These six amino acid residues comprise the Mac-1 receptor binding site of fibrinogen.

G. Preparation of a Polyclonal Anti-Polypeptide Receptor Binding Site Specific Antibody

1) Preparation of Immunogen

For preparation of a polypeptide immunogen, the synthetic polypeptide P1b (SEQ ID NO 13; Table 1) is prepared as described in Example 8B but is modified with a carboxy-terminal cysteine. The synthesized P1b is coupled to keyhole-limpet-hemocyanin (KLH) (Sigma, St. Louis, Mo.) using the heterobifunctional crosslinking agent, N-succinimidyl3-(2-pyridyldithio) propionate (SPDP)(Pierce Biochemicals, Rockford, Ill). For the coupling procedure, 80 microliters ($\mu$l) of 10 mg/ml SPDP dissolved in dimethylformamide is admixed dropwise to 400 $\mu$l 15 mg/ml KLH in 0.1M phosphate, 0.1M NaCl at pH 8.5 under continuous stirring conditions for 30 minutes at 22° C in order to form SPDP-activated KLH. The resultant SPDP-activated KLH is then extensively dialyzed at 4° C against a buffered solution of 0.1M phosphate and 0.1M NaCl at pH 7.4 in order to remove uncoupled SPDP. Six mg of prepared P1 having a C-terminal cysteine is first dissolved in 2 ml of 0.1M phosphate and 0.1M NaCl at pH 7.4 and then admixed with SPDP-activated KLH prepared above under continuous stirring conditions. The degree of coupling of P1b with KLH is monitored by the pyridine2-thione release at 343 nm ($\epsilon$: $8.08 \times 10^3$ $M^{-1}$ $cm^{-1}$) in a spectrophotometer.

2) Immunization and Collection of Polyclonal Antisera

The P1b-KLH immunogen prepared in Example 2a is emulsified using Adjuvant Complete Freund (DIFCO Laboratories, Detroit, Mich.) for the first injection and Adjuvant Incomplete Freund (DIFCO) for all subsequent injections according to the manufacturer's instructions, and the P1b-KLH antigens are incorporated into the emulsion at a concentration of 2 milligrams/milliliter (mg/ml). One-half ml of a prepared emulsion is injected subcutaneously into each of two New Zealand white rabbits after pre-immune serum samples are collected. The rabbits are injected three times at weekly intervals following the injection protocol as detailed. Two weeks after the last injection, blood samples are collected to check antibody titer against the P1 used as an immunogen by the ELISA assay described below. The collected blood samples are stored at 4° C. for 12 hours, after which the samples were centrifuged at 3000× g for 20 minutes. The resultant supernatant containing antipolypeptide receptor binding site specific antibodies are collected and stored at −20° C.

Peptides P1, DII, G7, G8 and G10 (Table 1) are also separately prepared as immunogens by conjugation with KLH as described above. Immunization of separate rabbits for the production of antisera against each of the peptides listed above is performed as described above. The resultant antisera are then screened by ELISA as described for anti-P1b receptor binding site specific antibody below.

3) ELISA to Screen Antisera Immunoreactivity

The peptide antibody titers and immunospecificity in sera collected from rabbits in Example 2b are determined in an enzyme-linked-immunosorbent-assay (ELISA). The antigens used in the ELISA include the immunizing polypeptide P1, $D_{30}$ and fibrinogen.

Briefly, 50 $\mu$l of either 50 $\mu$M P1b prepared in Example 1 or 10 $\mu$g/ml of $D_{30}$ or fibrinogen prepared in Example 1 in a buffer consisting of 0.05M sodium carbonate ($Na_2CO_3$) and 0.02% $NaN_3$ at pH 9.0 are admixed into the wells of microtiter plates. The plates are maintained at 37° C. for one hour to permit the antigens to become operatively affixed to the well walls. After washing the antigen-coated wells with TBS, the wells are blocked with 250 $\mu$l/well of 10% BSA in TBS for one hour at 22° C. The blocking solution is then removed and the wells are subsequently washed five times with 250 $\mu$l/well of maintenance buffer (0.05M Tris-HCl, 0.1 M NaCl, 0.02% NAN,, 1 mg/ml BSA, 5 mM $CaCl_2$, 0.01% Tween 20 at pH 7.4). Fifty $\mu$l of rabbit non-immune or specific antiserum serially diluted in maintenance buffer is then admixed to the washed wells and maintained for one hour at 37° C. to allow formation of a solid liquid phase immunoreaction products. The wells are then washed three times with maintenance buffer followed by admixture of 50 $\mu$l of 2.0 $\mu$g/ml of secondary antibody (polyclonal biotinylated goat-anti-rabbit-IgG) (Pierce Biochemicals, Rockford, Ill) diluted in maintenance buffer to each well for the detection of immunoreactant products. The plates are maintained for 1 hour at 37° C. after which time the secondary antibody solution is removed. After washing the wells as described above, 50 $\mu$l of 2.0 $\mu$g/ml streptavidin-alkaline-phosphatase (Pierce Biochemicals) in maintenance buffer is admixed into each well and maintained for 30 minutes at 37° C. Detection of specific immunoreaction products is obtained by admixture of 150 $\mu$l/well of 5 mg/ml p-nitrophenylphosphate (PNPP) (Pierce Biochemicals) in 0.1M diethanolamine and 0.02% $NaN_3$ at pH 9.6 followed by measurement of the change in absorbance at 405 nm over time using the EL312 Microplate Bio-Kinetics Reader and the KinetiCalc Software Program (Biotek Instruments, Inc., VT). Non-specific binding is considered as the measured absorbance in 10% BSA blocked wells which serves as negative controls without the preceding coating of a specific protein or polypeptide. Under the described conditions, non-specific binding never exceeds more than 5% of the specific binding. Rabbit antisera which exhibit significant immunoreactivity as compared to the pre-immune serum toward P1b, $D_{30}$ and fibrinogen are then selected for further purification as described below.

Rabbit antisera which are obtained above against polypeptides P1, DII, G7, G8 and G10 are screened for immunoreactivity to the respective polypeptide immunogens and $D_{30}$ and fibrinogen as described above. Rabbit antisera which exhibit significant immunoreactivity as compared to the pre-immune serums toward the polypeptide immunogen and $D_{30}$ and fibrinogen are further purified and analyzed as described below.

4) Purification of Anti-P1b Receptor Binding Site Specific Antibody

Purification of the IgG fraction from rabbit antiserum, which showed significant reactivity towards P1b is achieved by ammonium-sulfate precipitation (0–45%), followed by purification of IgG on an ion-exchange Mono Q column (Pharmacia) connected to a fast protein liquid chromatography (FPLC) system (Pharmacia). Immunoaffinity purification of the pooled immunoreactive IgG-fraction is performed by passing the IgG over a 3-ml column of $D_{30}$ prepared in Example 1 (3.4 mg of immunoaffinity-purified PC/ml gel) coupled to Sepharose 4B (Pharmacia) according to manufacturer's instructions. After thorough washing of the column with 5 column volumes of 0.05M Tris-HCl and 1 M NaCl at pH 7.4 to remove unbound antibodies, the bound IgG is eluted with two column volumes of 0.1 M glycine-HCl at pH 2.5. The eluted protein is monitored by absorbance at 280 nm and the IgG concentrations determined from the extinction coefficient of 13.5. The eluted IgG is immediately dialyzed against TBS-Az, concentrated against 50% sucrose and once more extensively dialyzed against TBS-Az. The purity of the resultant IgG is assessed by 4–15% SDS-PAGE. This immunoaffinity-purified anti-polypeptide antibody is then useful in this invention as an anti-polypeptide receptor binding site specific antibody.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. An isolated, purified polypeptide having a length of no more than 150 amino acid residues, which polypeptide is a fragment of the $D_{30}$ region of the gamma chain of fibrinogen (SEQ ID NO 3), wherein said fragment includes an amino acid residue sequence represented by the formula —QKRLDGS—, said sequence shown in SEQ ID NO 3 from residue 195 to residue 201.

2. The polypeptide of claim 1, wherein said polypeptide has an amino acid residue sequence represented by a formula selected from the group consisting of:

QKRLDGSVDFKK (SEQ ID NO 3: 195–206),

GQKRLDGSVDFKK (SEQ ID NO 11: 195–206),

WTVFQKRLDGSV (SEQ ID NO 3: 191–202),

GQKRLDGS (SEQ ID NO 11: 195–201),

QKRLDGS (SEQ ID NO 3: 195–201),

KYGWTVFQKRLDGSV (SEQ ID NO 12: 191–202), and

KYGQKRLDGS (SEQ ID NO 13: 195–201).

* * * * *